US010099192B2

(12) United States Patent
Carrick et al.

(10) Patent No.: US 10,099,192 B2
(45) Date of Patent: Oct. 16, 2018

(54) POLYMER SHELLS

(75) Inventors: Christopher Carrick, Stockholm (SE);
Bert Pettersson, Stockholm (SE); Lars Wågberg, Lidingö (SE); Marcus Ruda, Bandhagen (SE)

(73) Assignee: Cellutech AB, Stockholm (SE)

( * ) Notice: Subject to any disclaimer, the term of this patent is extended or adjusted under 35 U.S.C. 154(b) by 397 days.

(21) Appl. No.: 13/144,916

(22) PCT Filed: Feb. 9, 2010

(86) PCT No.: PCT/SE2010/050152
§ 371 (c)(1),
(2), (4) Date: Nov. 15, 2011

(87) PCT Pub. No.: WO2010/090594
PCT Pub. Date: Aug. 12, 2010

(65) Prior Publication Data
US 2012/0053250 A1 Mar. 1, 2012

Related U.S. Application Data

(60) Provisional application No. 61/150,805, filed on Feb. 9, 2009, provisional application No. 61/150,806, filed on Feb. 9, 2009.

(30) Foreign Application Priority Data

Feb. 9, 2009 (SE) .................... 0950061-2

(51) Int. Cl.
*B01J 13/02* (2006.01)
*B01J 13/04* (2006.01)
*B01J 13/06* (2006.01)
*A61K 9/50* (2006.01)
*B01J 20/285* (2006.01)
*B01J 20/286* (2006.01)
*B01J 20/32* (2006.01)

(52) U.S. Cl.
CPC ............ *B01J 13/06* (2013.01); *A61K 9/5036* (2013.01); *A61K 9/5042* (2013.01); *A61K 9/5089* (2013.01); *B01J 20/285* (2013.01); *B01J 20/286* (2013.01); *B01J 20/3268* (2013.01); *B01J 20/3274* (2013.01); *B01J 20/3293* (2013.01)

(58) Field of Classification Search
CPC ..... B01J 3/00; B01J 4/001; B01J 13/02; B01J 13/06; B01J 13/08
USPC ............... 264/4.6, 4.7; 427/213.3; 536/56
See application file for complete search history.

(56) References Cited

U.S. PATENT DOCUMENTS

| 2,773,027 A | 12/1956 | Powers et al. |
| 3,197,450 A * | 7/1965 | Tsou ..................... C08F 8/12 525/62 |
| 3,558,507 A | 1/1971 | Harbort |
| 3,660,304 A * | 5/1972 | Hiroharu et al. ............ 264/4.3 |
| 3,784,475 A * | 1/1974 | Diehl et al. .................. 510/361 |
| 4,859,711 A | 8/1989 | Jain et al. |
| 5,047,180 A | 9/1991 | Steiner et al. |
| 5,223,370 A * | 6/1993 | Sacripante et al. ........ 430/109.3 |
| 5,424,336 A | 6/1995 | Taniguchi |
| 5,487,390 A | 1/1996 | Cohen et al. |
| 6,368,662 B1 * | 4/2002 | McDaniel et al. ........... 427/216 |
| 6,395,301 B1 * | 5/2002 | Cantin ................ A61K 8/0208 206/581 |
| 7,056,554 B2 | 6/2006 | Voigt et al. |
| 7,081,139 B2 * | 7/2006 | Joerger et al. ............... 8/115.54 |
| 2003/0017194 A1 * | 1/2003 | Joerger .................. A01N 43/16 424/443 |
| 2003/0118664 A1 | 6/2003 | Trogolo et al. |
| 2003/0175517 A1 | 9/2003 | Voigt et al. |
| 2007/0031504 A1 | 2/2007 | Lien et al. |
| 2007/0219141 A1 * | 9/2007 | Jones et al. .................... 514/22 |

FOREIGN PATENT DOCUMENTS

| EP | 1448840 B1 | 1/2007 |
| GB | 1 364 815 | 8/1974 |
| JP | 50-6229 | 1/1975 |
| JP | S51-125675 | 11/1976 |
| JP | H05-228359 | 9/1993 |
| JP | 2003-514650 | 4/2003 |
| JP | 2004-504931 | 2/2004 |
| JP | 2006-111789 | 4/2006 |

(Continued)

OTHER PUBLICATIONS

Gaud et al. (Natural Excipients, Second Edition, published Jan. 2008, p. 4.36).*
Utada et al., "Monodisperse Double Emulsion Generated from a Microcapillary Device", Science, vol. 308, Apr. 22, 2005, pp. 537-541.
International Search Report received for PCT Patent Application No. PCT/SE2010/050152, dated Jun. 23, 2010, 8 pages.
International Preliminary Report on Patenetability received for PCT Patent Application No. PCT/SE2010/050152, dated Aug. 9, 2011, 12 pages.
Soppimath et al., "Effect of Coexcipients on Drug Release and Floating Property of Nifedipine Hollow Microspheres: A Novel Gastro Retentive Drug Delivery System", Journal of Applied Polymer Science, vol. 100, 2006, pp. 486-494.

(Continued)

Primary Examiner — Alma Pipic
(74) Attorney, Agent, or Firm — Fish & Richardson P.C.

(57) ABSTRACT

The present invention relates to a method for the preparation of polymer shells, preferably composed of cellulose or hemicellulose, comprising the steps of dissolving the polymer component in a first solvent, preferably an organic solvent and precipitating the polymer component by contacting the first solution with a second solvent, which second solvent has a polar character, and in which second solvent the polymer component is essentially insoluble, thereby obtaining polymer shells. Moreover, the invention refers to the polymer shells as such, having permeable and responsive properties, as well as various applications comprising such polymer shells within the fields of drug delivery, separation techniques, and inter alia filling material.

11 Claims, 15 Drawing Sheets

(56) References Cited

FOREIGN PATENT DOCUMENTS

| JP | 2007-196223 | | 8/2007 |
|---|---|---|---|
| JP | 2008-161817 | | 7/2008 |
| JP | 2010-504931 | | 2/2010 |
| SE | 358908 | | 8/1973 |
| WO | WO-95/19184 | | 7/1995 |
| WO | 95/23615 | * | 9/1995 |
| WO | WO-03/064509 | | 8/2003 |
| WO | 2006/110802 A1 | | 10/2006 |
| WO | WO-2008/037470 | | 3/2008 |
| WO | 2008/104528 A2 | | 9/2008 |
| WO | 2008/104528 A3 | | 9/2009 |

OTHER PUBLICATIONS

Office Action received for Japanese Patent Application No. 2011-549125, dated Nov. 12, 2013, 14 pages. (9 pages of English translation and 5 pages of Official copy).

Kondo et al., "Micro Capsule <Function and Application thereof>", Nippon Kikaku Kyokai, 1st printing of 1st Edition, Mar. 20, 1991, pp. 228-229 (Partial English translation provided). Translated p. 228.

Kondo et al., "Micro Capsule-Production Method, Properties, Application thereof", Sankyo Shuppan K.K., 2nd Printing, Nov. 25, 1978, pp. 1-14 (Partial English translation provided). Translated p. 6 lines 5-18 and 19-20.

Notice of Reasons for Refusal (translation) for JP 2011-549125, Oct. 28, 2014, 6 pages.

Supplementary European Search Report for EP 10738824.1, dated Jun. 27, 2014, 11 pages.

Communication pursuant to Article 94(3) EPC for 10 738 824.1 dated Dec. 2, 2015, 5 pages.

Communication for EP 10738824.1, dated Oct. 24, 2016, 5 pages.

Debeaufort et al., "Edible films and coatings: Tomorrow's packagings: A review," Critical Reviews in Food Science (1998) 38(4):299-313.

Decision of Allowance for KR 10-2011-7017701, dated Oct. 31, 2016, 2 pages.

Office Action for JP 2011-549125, dated Nov. 17, 2017, 1 page.

Office Action for KR 10-2011-7017701, dated Jan. 27, 2016, 14 pages (English translation included).

* cited by examiner

POLYMER SHELLS

CROSS REFERENCE TO RELATED APPLICATIONS

This is a U.S. National Phase patent application of PCT/SE2010/050152, filed Feb. 9, 2010, which claims priority to Swedish Patent Application No. 0950061-2, filed Feb. 9, 2009, and to U.S. Provisional Patent Application No. 61/150,805, filed Feb. 9, 2009, and U.S. Provisional Patent Application No. 61/150,806, filed Feb. 9, 2009, each of which is hereby incorporated by reference in the present disclosure in its entirety.

FIELD OF THE INVENTION

The present invention relates to a method for the preparation of polymer shells, insoluble in polar solvents, with permeable, responsive properties, the polymer shells as such, as well as various applications comprising such polymer shells within the fields of drug delivery, separation techniques, and inter alia filling material.

TECHNICAL BACKGROUND

Numerous biopolymers exhibit appealing characteristics for many industrial applications, for instance within the paper and textile industries but also within the pharmaceutical sciences and within various types of separation processes. Cellulose and hemicellulose are extensively characterized biopolymers of great significance not only as a basis for paper and textile manufacture but increasingly as drug delivery vehicles, for biomedical and biotechnological purposes, as well as solid phase component for various chromatographic separation techniques. The straight-chain hydrophilic cellulose possesses several interesting properties for pharmaceutical applications, for instance an absence of immunostimulatory properties and insusceptibility to enzymatic breakdown within the human body. Furthermore, its high mechanical rigidity has resulted in the use of cellulose as stationary phase for numerous separation applications.

Concomitant with the emergence of biotechnologically developed pharmaceuticals such as proteins, peptides, siRNAs, miRNAs, and antisense oligonucleotides, for the treatment of various diseases, the need for efficient delivery vehicles is greater than ever. Furthermore, improving delivery of conventional pharmaceuticals is in many cases critical in order to be able to increase dosage, decrease side effects, and improve pharmacokinetic properties. Encapsulating a drug of interest in a polymer shell is one way of improving its pharmacokinetic and possibly also its pharmaocodynamic properties, providing for instance sustained release over longer periods of time, formulations for local delivery, or protecting the drug from the harsh gastrointestinal environment or enzymatic breakdown upon per os administration.

Efficient separation processes are of vital importance within many industries, both for analytical and preparative purposes. The chemical industry, the pulp and paper industry, the petrochemical industry, as well as the medical and the pharmaceutical industries, among others, rely heavily on numerous separation process methodologies for various objectives. Separation is often based on chromatographic principles, i.e. passing the analyte-containing sample through a stationary, solid phase, in order to separate the components of the sample. The stationary phase is often composed of a polymeric material that exhibits certain properties forming the basis for the separation, for instance hydrophobicity, size, or ionic charge. The solid stationary phase furthermore needs to possess excellent characteristics in terms of, for instance, mechanical strength, chemical inertness and uniform size, in order to make the separation reliable and reproducible. Polymer shells are increasingly utilized as solid phase materials, as they possess many of the abovementioned characteristics, as well as the highly desired property of being able to function as a membrane with selective permeability for release and uptake of various molecules.

Polymer fibres for various purposes have long been produced using numerous techniques, but the preparation of shells, hollow substantially spherical particles, is still a complicated procedure. Cellulose fibres in the form of viscose have for instance been spun for almost a decade but a similar production of shells in a fast and reliable way naturally poses significantly more intricate problems. Spinning of fibres is normally based on applying a pressure on a dissolved polymer material and consequently forcing it out from a nozzle and into a bath where the fibres are formed, as a result of various chemical interactions. This approach is as of yet not possible for the production of polymer shells, as this would require the lumen of the fibres to be systematically divided. Currently, polymer shells based on cellulose are normally prepared in emulsions using methods relying on solvent diffusion and evaporation, an inefficient and to a certain extent time-consuming process, requiring the presence of additional coexcipients, such as polyethylene glycol, dibutyl phthalate, and polycaprolactone. Hollow beads composed of modified cellulose are also produced based on drop-wise addition to precipitation baths containing metal ions, resulting in subsequent precipitation of metal salts of polymer. This method, however, requires the beads to be cured in a curing bath containing additional metal ions. From a drug delivery perspective, the noticeable presence of metal ions may be a limiting aspect, possibly resulting in allergic reactions and undesired in vivo interactions. Furthermore, utilizing such shells for chromatographic purposes may limit the applicability only to certain types of separation, for instance based on ionic charge properties.

The polymer shells based on cellulose described in the prior art relate to non-responsive shells essentially displaying identical characteristics irrespective of the surrounding conditions. In order to prepare efficient drug delivery vehicles or stationary phase components of chromatographic systems, it is desirable to utilize shells with dynamic responsive properties. The ability to modulate, for instance, the permeability, the diameter, and the volume of polymer shells, would provide additional advantages e. g. increasing the release of a pharmaceutical composition upon exposure to certain external conditions, or modulating the properties of a chromatography column depending on the characteristics of the sample. Polymer shells displaying such characteristics are hitherto lacking in the prior art.

There is thus a need in the art for a rapid, simple, versatile, and robust manufacturing method without the use of excessive amounts of harsh chemicals for the preparation of polymer shells with responsive modifiable properties, for instance for drug delivery or chromatography purposes. Furthermore, carbohydrate polymer shells essentially only comprising the carbohydrate in question, resulting in minimized immunostimulatory properties and increased versatility within the field of chromatography, are lacking in prior art.

Prior art, SE 358 908, teaches the manufacture of hollow cellulose fibres, through spinning of viscose. The invention discloses a spinning bath containing a high concentration of magnesium ions, exerting a reducing effect on the swelling properties of the polymer when spinning viscose fibres through nozzles into said spinning bath.

U.S. Pat. No. 2,773,027 discloses a method for preparing hollow beads consisting of a metal salt of carboxymethyl cellulose, for use as a dialysis medium. An aqueous solution of carboxymethyl cellulose is drop-wise transferred into a precipitation bath consisting of a metal salt in an aqueous solution, wherein the metal salt-carboxymethyl cellulose beads are precipitated.

Soppimath and coworkers (Soppimath et al., 2006, Journal of Applied Polymer Science, 100, 486-494) describe a method based on the solvent-evaporation technique for the preparation of floating hollow microspheres using modified cellulose. Excipients such as polyethylene glycol, dibutyl phthalate, and polycaprolactone are utilized for the formation of the microspheres, with ethyl acetate acting as a dispersing solvent.

As an example of an efficient modification of the solvent evaporation technique, Utada and colleagues (Utada et al., 2005, Science, 308, 537-541) disclose a microcapillary device for generating monodisperse double emulsions containing a single internal droplet in a core-shell geometry, with a high degree of control and flexibility. The microcapillary system is further employed for the generation of polymeric vesicles using a water-in-oil-in-water emulsion comprising the diblock copolymer poly(butyl acrylate)-b-poly(acrylic acid) (PBA-PAA).

SUMMARY OF THE INVENTION

It is the object of the present invention to overcome said drawbacks and satisfy the existing needs, as well as providing a simplified method for the preparation of polymer shells. Therefore, the present invention is concerned with a method for preparing polymer shells, insoluble in polar solvents and comprising essentially only cellulose/hemicellulose, exhibiting responsive modifiable properties, the shells as such, and various applications of such shells for drug delivery purposes, for a range of analytical and preparative separation techniques, and for a number of applications as filling and/or packaging material.

More specifically, the method comprises the steps of dissolving the polymer component in a first solvent, preferably an organic solvent and precipitating the polymer component by contacting the first solution with a second solvent, which second solvent has a polar character, and in which second solvent the polymer component is essentially insoluble, thereby obtaining polymer shells. The method enables the rapid, scalable, and robust formation of polymer shells, essentially only comprising the polymer in question, with responsive modifiable properties without the use of additional excipients or curing baths.

| # | Item |
| --- | --- |
| (5) | Reaction chamber |
| (10) | Injection tube |
| (15) | Collecting tube |
| (20) | Fluid 1 |
| (25) | Fluid 2 |
| (30) | Fluid 3 |

Figure 10:
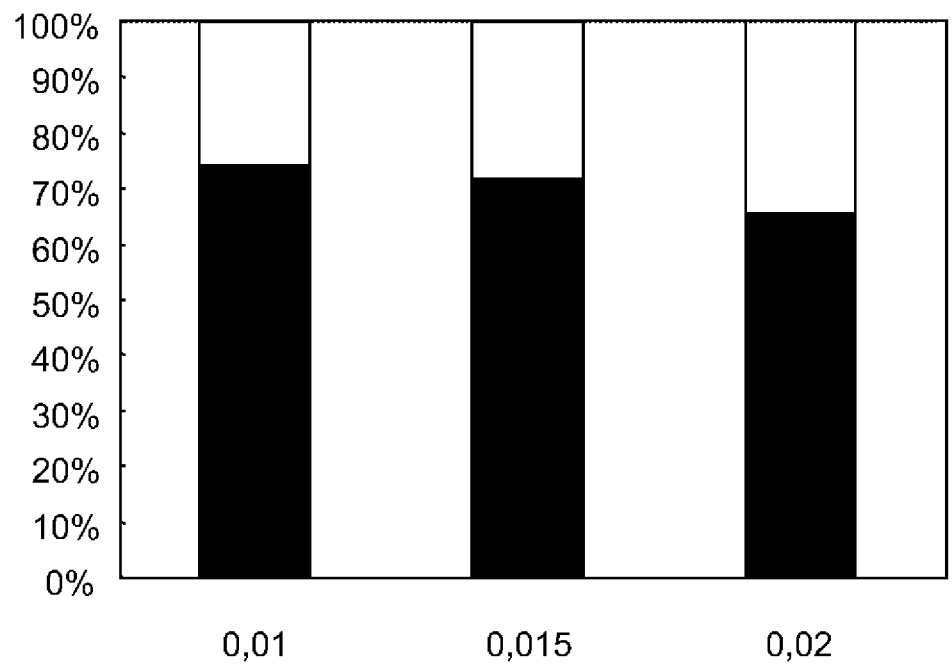
Figure 11:
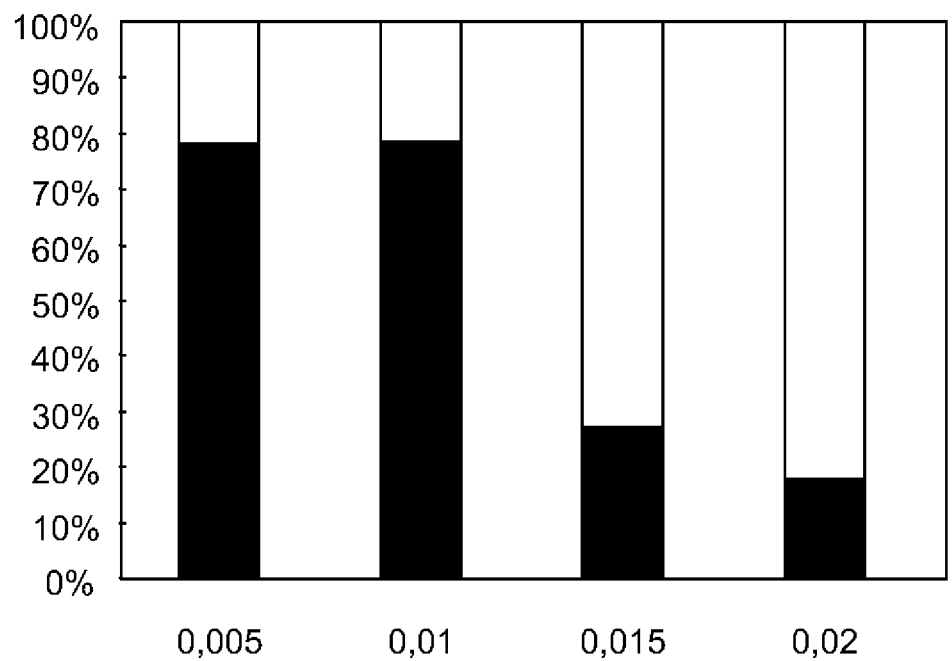
Figure 12:
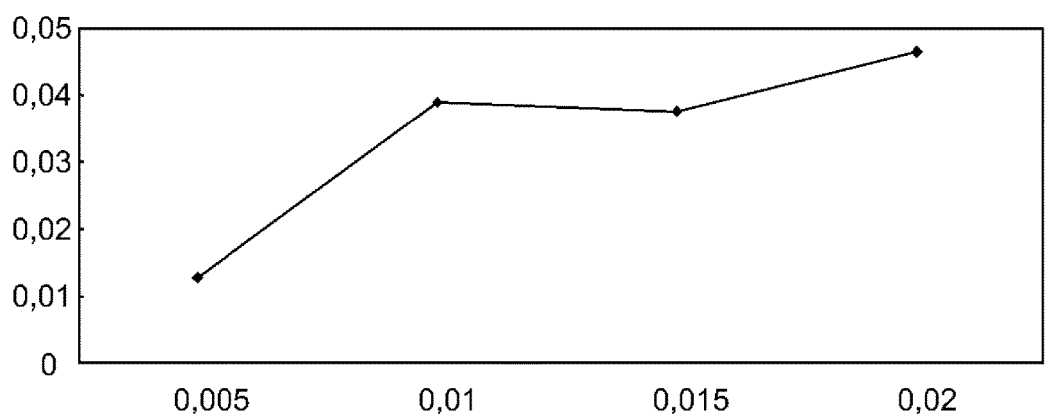

FIG. 10 shows the relationship between the wall thickness and the space inside the polymer shells when feeding carbon dioxide into the solution during 30 minutes. X-axis: % Dissolving pulp in the cellulose solution. Y-axis: Constituent of the shell. White bar corresponds to wall thickness. Black bar corresponds to hollow space FIG. 11 plots the relationship between the wall thickness and the space inside the polymer shells when feeding carbon dioxide into the solution during 5 minutes. X-axis: % Dissolving pulp in the cellulose solution. Y-axis: Constituent of the shell. White bar corresponds to a all thickness. Black bar corresponds to hollow space FIG. 12 shows the relationship between the density (kg/$dm^3$) and polymer concentration (weight %) of the polymer shells. X-axis: Cellulose concentration (weight %) Y-axis: Density (kg/dm3)

FIGS. 13A, 13B, 16A, 16B and 16C display scanning electron microscopy (SEM) pictures of 1% cellulose shells, as well as magnified views of the shell wall.

FIGS. 14A, 14B, 15A, 15B, 17A, 17B and 17C show SEM pictures of 1.5% cellulose shells, as well as magnified views of the shell wall.

FIGS. 18A, 18B and 18C display SEM pictures of a 2% cellulose shell, as well as magnified views of the shell wall.

FIG. 19A, FIG. 19B, FIG. 19C, and FIG. 19D display SEM pictures of microwave dried shells.

Figure 20:
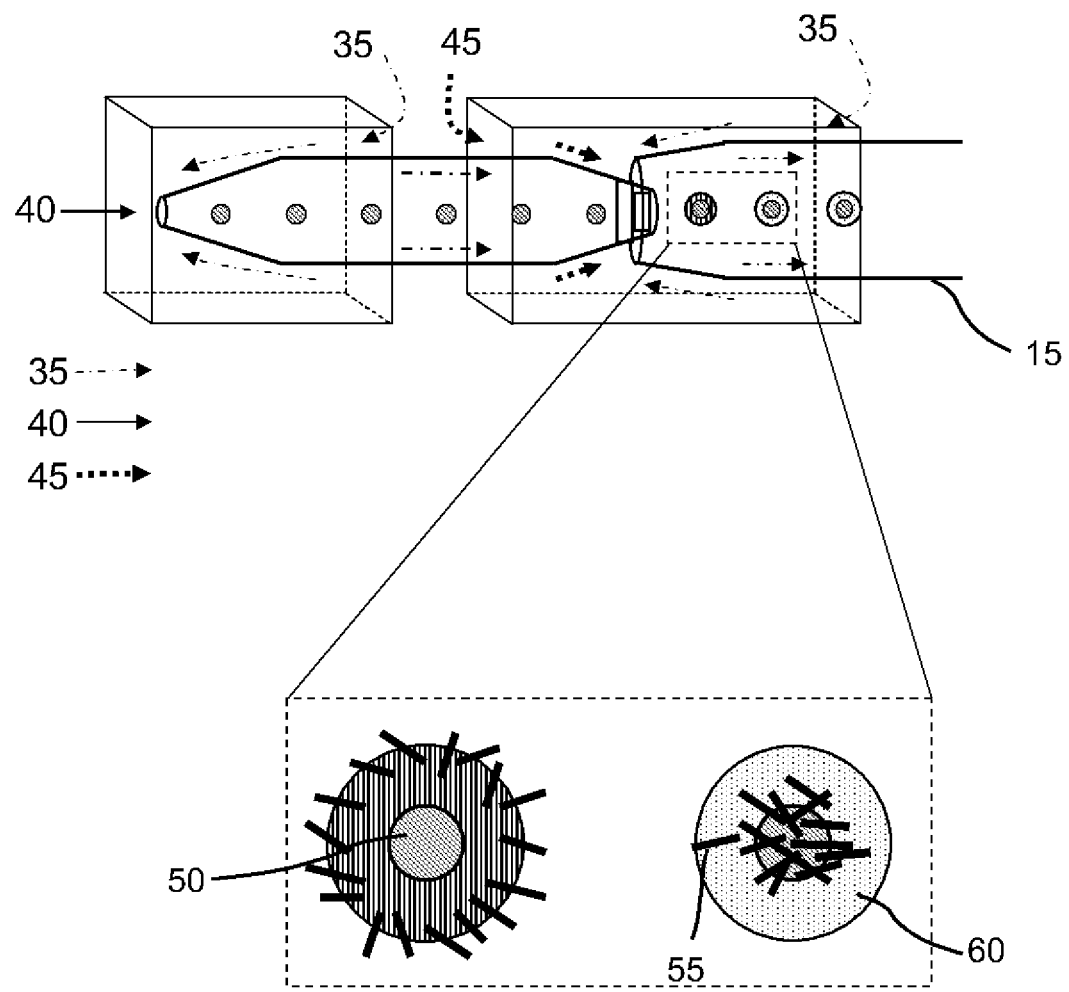

FIG. 20 portrays microfluidic reaction chambers that may be utilized for the present invention, with a magnified view of the polymer shells; for instance with the following items present:

| # | Item |
|---|---|
| (5) | Reaction chamber |
| (10) | Injection tube |
| (15) | Collecting tube |
| (35) | Arrow indicating flow of PDMS oil |
| (40) | Arrow indicating flow of water |
| (45) | Arrow indicating flow of polymer fluid |
| (50) | Water |
| (55) | Polymer |
| (60) | PDMS oil |

DETAILED DESCRIPTION OF THE INVENTION

The present invention is concerned with a method for preparing polymer shells, insoluble in polar solvents and essentially only comprising preferably cellulose/hemicellulose, exhibiting responsive modifiable properties, the shells as such, and various applications of such polymer shells for drug delivery purposes and for a range of analytical and preparative separation techniques.

As will be apparent from the description and the examples, the term "shells" relates to any structure, with dimensions of between 0.1 µm and 10 mm, substantially encasing any space, containing either gaseous, liquid, and/or solid material, and comprising at least one polymer material comprising for example a carbohydrate material of repeated units of polysaccharides, for instance cellulose or hemicellulose or any other polysaccharide with properties that can be expected to be similar to the properties of cellulose and hemicellulose, or chitosan, galactoglucomannan, and/or any derivatives thereof. The term "space" relates to any volume defined by any regular or irregular geometric shape, arising upon encasing by said shell, comprising either a gas and/or a liquid and/or a solid.

Where features, embodiments, or aspects of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups.

One aspect of the method of the invention comprises the steps of providing a suitable polymer component and dissolving it in a first solvent, preferably a non-polar solvent, optionally mixing a core-forming substance in the solution comprising the polymer component, such as by dissolving gas in the first solution or by pressurizing the first solution, in order for the core-forming substance to form cores, in which the polymer component is essentially immiscible. Subsequently, the polymer component is precipitated through contacting the first solution with a second solvent, said second solvent having a polar character in which the polymer component is essentially insoluble, thereby obtaining polymer shells, optionally formed around said cores.

The polymer component can be any polymer, either natural or synthetic, substantially inert or biologically active, for instance a polysaccharide such as cellulose or hemicellulose or any other polysaccharide with properties that can be expected to be similar to the properties of cellulose and hemicellulose, or chitosan, galactoglucomannan, glycosaminoglycan, heparin sulphate, hyaluronan, chondroitin sulphate, or a proteoglycan, a polyester, a polyether, a polyvinyl, or the like or any derivative thereof.

The first solvent can be any solvent in which the polymer is dissolved, such as an organic solvent, e.g. dimethylacetamide (DMAc) or N-methyl morpholine oxide (NMMO).

The second solvent has preferably a polar character so that the polymer is insoluble therein, e.g. water, methanol, ethanol, isopropanol, 1,2-dichloroethane, and/or toluene, or the like. Utilizing water (polar index 9), ethanol (polar index 5.2), 1,2-dichloroethane (polar index 3.5) or toluene (polar index 2.4), or any combinations of these solvents results in almost immediate precipitation and formation of cellulose shells, whereas the use of cyclohexane (polar index 0.2) appears to result in slower shell formation, implying that the rapid precipitation of the polymer shells, at least when utilizing cellulose, stops somewhere in the interval between 0.2 and 2.4.

By "mixing a core-forming substance" is meant that a substance or element that has the capacity to form a core, e.g. in the form of bubbles, such as carbon dioxide, air, argon, nitrogen, hydrogen, and/or Liquefied Petroleum Gas (LPG; 40% butane and 60% propane), or the like, is introduced to the polymer solution, e.g. by feeding gas into the solution, or by pressurizing the solution, and thereby solubilising the gas in the solution. Other core-forming substances within the spirit of the present invention may for instance pertain to liquids and/or solids and/or emulsions capable of forming cores. Further, the core-forming substances may additionally comprise various active substances.

An embodiment of the method of the present invention comprises the steps of providing a suitable polysaccharide material, for instance cellulose or hemicellulose, or any other polysaccharide with properties that can be expected to be similar to the properties of cellulose and hemicellulose, or chitosan, galactoglucomannan, or any derivative thereof, optionally washing the polymer component repeatedly in water, methanol, and dimethylacetamide (DMAc) or any other organic solvents before dissolving it in a first solution comprising at least one organic solvent, preferably DMAc, and at least one type of metal ion, preferably an alkali metal ion. Another organic solvent within the scope of the invention is N-methyl morpholine oxide (NMMO), but the use of this solvent necessitates an absolute absence of metal ions. The amount of polymer dissolved in the solution generally ranges from approximately 0 to 25% w/w, but preferably from 0 and 5% w/w, depending on the characteristics of the selected polymer, especially molecular weight, degree of substitution, and the nature of the substituents. The metal ion in the organic solvent (for example DMAc) disturbs intra- and intermolecular hydrogen bonding between the polymer(s), increasing its solubility. Lithium ions are preferred, but other alkali metal and metal ions may also be employed, for instance Mg, Na, Fe, Al, and Cu. The concentration range is preferably between 0.1 to 25% w/w and even more preferably between 5 and 10% w/w. Optionally, a core-forming substance is mixed in to the solution in order to aid the formation of cores for improved generation of the polymer shells, such as by addition of a liquid and/or a solid and/or a gas, for instance by feeding a suitable gas into the first solution or by pressurizing the first solution with a suitable gas, for instance carbon dioxide, air, argon, nitrogen, hydrogen, and/or LPG, to further facilitate the formation of cores, and finally the polymer solution is transferred to a second solution comprising solvent of a polar character in which the polymer component is insoluble, and consequently where the polymer shells, insoluble in said second solvent, are precipitated and formed.

In another embodiment, the method for preparing polymer shells comprises dissolving the polymer component in a first solvent and subsequently mixing a core-forming substance into said polymer-containing solution. The core-forming substance may be selected from the group comprising at least one gas, at least one liquid, and/or at least one solid, inter alia $CO_2$, air, argon, nitrogen, hydrogen, LPG, water, hexane and/or any other hydrocarbon, and/or PDMS and/or any other polysiloxane. Finally, the polymer shells are formed through precipitating the polymer component by contacting the first solution with a second solvent, which second solvent has a polar character, and in which second solvent the polymer component is essentially insoluble, thereby obtaining polymer shells, optionally formed around said cores.

A further embodiment of the present invention discloses a method for preparing transparent, hard, springy polymer shells, comprising an additional step of microwave drying the polymer shells after the precipitation, thereby obtaining transparent, springy shells, preferably comprising cellulose and/or hemicellulose, or other polymers with similar properties. The microwave drying may be carried out in a domestic microwave oven, for instance at between 50 and 1500 W, preferably approximately at 800 W. The drying may be carried out for anywhere between 10 seconds and several hours, depending on the drying conditions and the shells per se. The polymer shells resulting from the above method possess highly interesting physical properties, for instance springiness (i. e. upon releasing an applied physical pressure, the shells return to their original shape), stiffness, and transparency.

Another embodiment of the present invention discloses a method comprising the steps of providing a suitable polysaccharide material, for instance cellulose or hemicellulose, or any other polysaccharide with properties that can be expected to be similar to the properties of cellulose and hemicellulose, or chitosan, galactoglucomannan, or any derivative thereof, washing the polymer component repeatedly in water, methanol, and dimethylacetamide (DMAc) or any other organic solvents before dissolving it in a first solution comprising at least one organic solvent, preferably DMAc, and at least one type of metal ion, preferably an alkali metal ion. The amount of polymer dissolved in the solution generally ranges from approximately 0 to 25% w/w, but preferably from 0 and 5% w/w, depending on the characteristics of the selected polymer, especially molecular weight, degree of substitution, and the nature of the substituents. The metal ion in the organic solvent (for example DMAc) disturbs intra- and intermolecular hydrogen bonding between the polymer(s), increasing its solubility. Lithium ions are preferred, but other alkali metal and metal ions may also be employed, for instance Mg, Na, Fe, Al, and Cu. The concentration range is preferably between 0.1 to 25% w/w and even more preferably between 5 and 10% w/w. Optionally, a core-forming substance is mixed in to the solution in order to aid the formation of cores for improved generation of the polymer shells, such as by addition of a liquid and/or a solid and/or a gas, for instance by feeding a suitable gas into the first solution or by pressurizing the first solution with a suitable gas, for instance carbon dioxide, air, argon, nitrogen, hydrogen, and/or LPG, to further facilitate the formation of cores. Subsequently, the first solution is heated, in order to evaporate any water present in the solution, followed by exposure to a gas, either through increased pressure or through feeding a gas into the solution and thereby dissolving it, thus causing the formation of cores comprising either a gas and/or a liquid and/or a solid. The exposure to increased pressure is achieved either through pressurizing the solution with a suitable gas, thereby dissolving the gas in the polymer solution, or through forcing said solution through at least one capillary or capillary system and/or a microfluidic device. Finally, the polymer solution is transferred to a second solution comprising solvent of a polar character in which the polymer component is essentially insoluble, and consequently where the polymer shells, insoluble in said second solvent, are precipitated and formed, optionally around said cores. Polymer material suitable for the present invention may for example comprise cellulose or hemicellulose, or any other polysaccharide with properties that can be expected to be similar to the properties of cellulose and hemicellulose, or chitosan, galactoglucomannan, and/or any derivative thereof. The polymer material preferably comprises repeating units of one or more saccharides, but other carbohydrate and non-carbohydrate polymer materials are also within the scope of the invention. The polymer material is essentially in a disordered, amorphous form, but may also occur in crystalline form, or a mixture of the two. In one embodiment of the present invention, the polymer material may be dissolved in the metal ion/organic solvent solution in a concentration ranging from 0 to 25% w/w, preferably in a concentration range between 0 to 5% w/w. According to the invention, several types of wood pulps can be utilized in a substantially unmodified form, providing a distinct advantage over most existing technologies. The polymer content of the shells do not appear to affect their outer diameter, but increasing polymer concentration in the solvent leads to increased wall thickness and density, albeit not in linear fashion. Without wishing to be bound by any particular theory, it is surmised that increased polymer concentration in solution provides larger amounts of accessible building material, resulting in shells with thicker walls and higher density. Alternatively, the higher polymer content in solution may increase the viscosity and thereby prolong the gas dissolution time. The relationship between wall density and the hollow space inside the polymer shells, when feeding carbon dioxide into a cellulose solution during 30 minutes (FIG. 10), shows that the wall thickness increases slightly over a cellulose interval of between 1% and 2%. However, when feeding carbon dioxide into the solution for only 5 minutes (FIG. 11), the wall thickness increases significantly over a cellulose interval of between 0.5% and 2%. Taken together, the different wall thickness and shell density may affect shell characteristics, for instance mechanical properties and diffusion rate. Thus, the present invention can endow polymer shells with responsive physical properties, a highly sought after feature within many fields of application.

In one embodiment of the present invention, the metal or alkali metal ion concentration in the first solvent is between 0.1 to 25% w/w, preferably between 5 to 10% w/w. The alkali metal ion or the metal ion preferably comprises lithium, but other ions, known to a person skilled in the art, for example, Mg, Na, Fe, Cu, Al, Ni, Zn, K, Be, may also be utilized.

In another embodiment of the invention, the gas for pressurizing the first solution is carbon dioxide, but other suitable gases known to a person skilled in the art, for instance air, argon, nitrogen, hydrogen, and/or LPG, can also be used to facilitate the formation of the polymer shells.

According to the invention, the pressurized metal ion/organic solvent solution comprising the polymer material aids the formation of the shells when entering the second, precipitation, solution. When the pressurized first polymer solution is added to the non-solvent, i.e. the solvent of a polar character comprising polar solvent, the polymer, upon contact with the polar solvent, begins to precipitate and a gas bubble is nucleated within the polymer droplet. The higher pressure within the nucleated bubble, within the first polymer solution, results in an outward expansion of the polymer material when in contact with the second solution, leading to the formation of polymer shells. The use of LPG increased the space inside the polymer shells substantially compared to the other gases. Again without wishing to be bound by any theory, one possible explanation could pertain to the increased degree of dissolution of LPG in the polymer solution, implying that variations in a number of variables may endow the polymer shells with interesting, responsive properties.

In order to increase the spherical shape of the shells, the surface tension of the non-solvent wherein the precipitation occurs may be reduced, in one embodiment for instance with the use of surfactants, such as for instance amphoteric tensides, nonionic tensides, and/or anionic tensides. Again without wishing to be bound by any particular theory, it is surmised that the increased spherical shape of the polymer shells when adding surfactants to the precipitation bath stems from the reduced surface tension of the non-solvent, resulting in facilitated surface penetration and decreased impact implying that the spherical, droplet-like shape is preserved during precipitation.

In an additional embodiment of the present invention, the first solution is transferred to the second solvent as a result of a physical phenomenon, such as a pressure difference between the vessel for dissolution of the polymer and the precipitation bath, or nucleation of carbon dioxide. The equipment utilized in this embodiment comprises a vessel containing the polymer dissolved in the pressurized first solution comprising metal ion/organic solvent, a component for transferring the solution, and a receiving precipitation vessel containing a solution comprising solvent of a polar character where the polymer shells, insoluble in said polar solvent, are precipitated. In another embodiment of the present invention, a spray device is employed to transfer the first polymer solution to the second solvent for precipitation. The spray device is connected with the polymer solution and said solution is subsequently sprayed onto a solvent of polar character where the polymer shells, insoluble in said polar solvent, are formed. In a further embodiment of the invention, the first solution is transferred manually to the precipitation bath comprising the second solvent, using, for instance, a pipette or any other type of laboratory instrument for transporting liquid.

Figure 9:
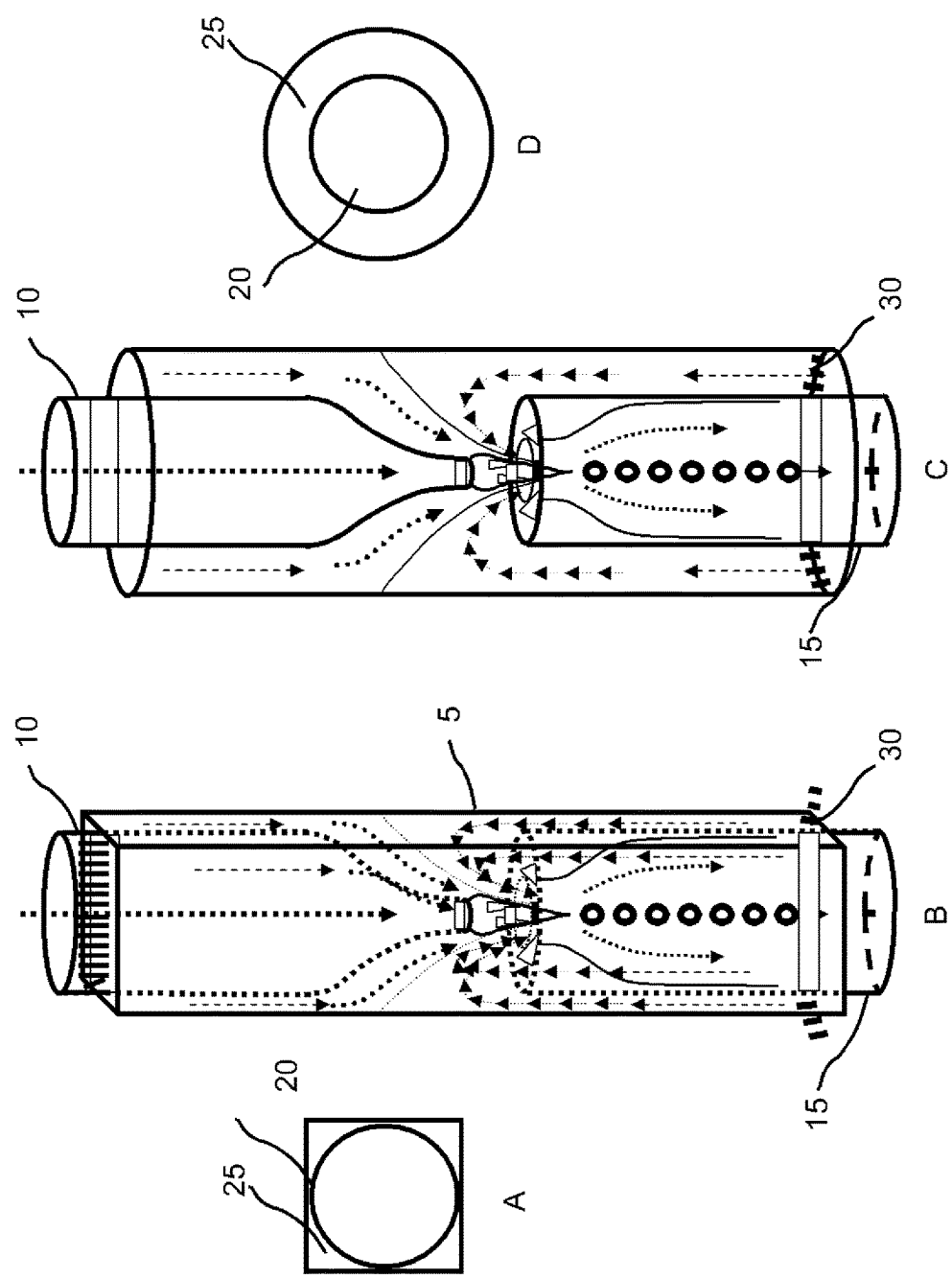
FIG. 9A is a top view of a microfluidic device in a rectangular reaction chamber.
FIG. 9B shows a microfluidic device in a rectangular reaction chamber.
FIG. 9C: Top view of a microfluidic device in a circular reaction chamber.
FIG. 9D shows a microfluidic device in a circular reaction chamber; with the-following items present.

In an additional embodiment, the methods described above are carried out in a microfluidic device and/or in a capillary system. A preferred embodiment of the present invention (see for instance FIG. 9) comprises two substantially cylindrical sequentially aligned microfluidic vessels, one injection tube containing an inner first solution and one collection tube containing an outer second solution of a polar character, partially encased in an outer container comprising the outer second fluid and a middle fluid. The middle fluid exerts a directing force on the inner polymer solution leaving the injection tube, resulting in the transfer of the inner polymer fluid into the second precipitation fluid, in which the polymer component and hence the polymer shells are insoluble, in the collection tube, where the polymer shells precipitate and form. Another embodiment of the present invention relates to a system of at least two sequentially assembled vessels connected via transferring components, where a sequential decrease in pressure from one vessel to the next results in transfer of the polymer solution from one vessel to the next, with precipitation of the polymer shells, insoluble in polar solvents, in a precipitation vessel.

A further embodiment teaches a method for preparing polymer shells, comprising the steps of dissolving the polymer component in a first solvent, and subsequently mixing the obtained solution obtained with a core-forming substance, wherein the core-forming substance is a water-in-oil emulsion. Finally, the polymer component is precipitated by contacting the first solution with a second solvent, wherein the second solvent is for instance water, optionally derived from the emulsion system, thereby obtaining polymer shells.

In one embodiment of the present invention, the solvent for dissolving the polymer is recovered and recycled after the precipitation of the polymer shells. In this particular embodiment of the invention, the solvent is NMMO, which is an efficient cellulose solvent only when concentrated. This implies that as the shells are precipitated, the NMMO is mixed with water and separated from the cellulose shells, and can thus be reused as a solvent by driving off the water. The absence of metal or alkali metal ions is in this case vital, to avoid explosions. In the use of DMAC/LiCl-mixture as polymer solvent, both chemicals can be reused after driving off the water. The use of this solvent mixture causes no risk of explosion in the presence of alkali metal ions.

According to one embodiment of the invention, polymer shells are formed in the presence of $CaCO_3$, resulting in shells comprising said compound and thereby exhibiting an interior space being substantially reversibly sealed. Upon exposure to low pH, the solubility of the $CaCO_3$ increases, leading to subsequent formation of pores in the polymer shells, facilitating diffusion and sustained release of a desired incorporated agent over at least several hours.

In yet another embodiment of the present invention, the fluid for precipitation of the polymer shells comprises polymers or compounds, soluble in the precipitation fluid, for coating of the surface of the shells to obtain a desired effect, for instance relating to sealing of the shells or functionalizing the surface. Such compounds can include but are not limited to, chitosan, galactoglucomannan, xyloglucan, and/or $CaCO_3$.

Another aspect of the invention relates to polymer shells substantially comprising carbohydrate polymers where the ratio of the inner diameter to the outer diameter of said shells is variable upon exposure to variable salt concentration and/or variable pH. According to the invention, the outer diameter and the thickness of the walls of the polymer shells, insoluble in polar solvents, both decrease when being left in solution over a pH range of 1 to 13 over a time frame of 2 to 3 hours, or until equilibrium has been reached.

According to the invention, an inwards radial swelling of the shell occurs as a result of variable pH and salt concentration, with the volume of the space inside the polymer shell increasing in volume with decreasing pH, and decreasing in volume with increasing salt concentration. According to the invention, the decrease in volume of the space inside the shell when increasing the pH is primarily a result of increasing thickness of the wall of the shell with increasing pH, and the decrease in volume of the space inside the shell with increasing salt concentration also originates from an increase in thickness of the wall of the shell when increasing the salt concentration. Consequently, according to the present invention, the swelling occurring upon exposure to variable salt concentration and variable pH results in inward radial expansion, with a relatively constant outer diameter, and the volume of the space inside the shell is inversely proportional to the salt concentration and the pH.

According to the invention, the initial thickness of the walls of the polymer shells increases with between 0.3 and 0.55 mm when increasing the pH from 1.5 to 10, depending on the polymer material. In a similar manner, the thickness of the walls of the shells increase, but more moderately, after 2 to 3 hours in solution, with the increase ranging from 0.2 to 0.25 mm over said pH interval. In yet another embodiment of the present invention, the thickness of the walls of the shells can be modulated depending on the degree of solubilisation of gas (i.e. the amount of gas dissolved) in the polymer solution. The present invention teaches methods for providing polymer shells, insoluble in polar solvents, with dynamic modifiable properties, the shells as such, and their applications. The fact that the chemical and physical properties of the shells can be controlled and modulated through such uncomplicated factors as variable salt concentration and variable pH, makes such shells highly desirable for many purposes, for instance within drug delivery and chromatographic separation, even though other usages, inter alia as packaging material, filling material, joint filling material, or as weathering, are within the spirit of the invention. According to one embodiment of the invention, a decrease in pH results in an increase in the volume of the space inside the shell, providing the shell with the characteristics of a pump or a membrane. In a similar manner, in one embodiment a decrease in salt concentration results in increase in volume of the space inside the shell. In other embodiments, the variation may be the opposite. Variable salt concentration and pH can be found within many biological, chemical, and physical systems, providing several fields of use for these polymer shells, insoluble in polar solvents. According to the present invention, higher pH induces ionization of functional groups on the polymer, resulting in swelling of the polymer material, leading to decreased volume of the space inside the shell. Further, when investigating polymers of different charge density, no apparent decrease in the volume of the space inside the cell was detected when increasing the pH, resulting in the conclusion that the water solubility of the gaseous carbon dioxide influences the properties of the shell. Upon entering of water into the shell, through capillary forces, at higher pH, the solubility of carbon dioxide is increased, reducing the outward gas pressure leading to a decreased volume of the space inside the shell.

The polymer shells, insoluble in polar solvents, according to the invention, are further characterized in that they possess an ability for sustained release of compounds over a timeframe ranging from approximately 0.1 hours to approximately 24 hours, preferably between 1 hour and 12 hours. Further according to the invention, these properties are modifiable upon varying the salt concentration and/or the pH, and the presence of additional polymers, and/or compounds attached to or incorporated in the shell, also influences the release properties.

The polymer material of the polymer shell may comprise cellulose, hemicellulose, chitosan, galactoglucomannan, or any derivative thereof. The polymer material preferably comprises repeating units of one or more saccharides, but other carbohydrate and non-carbohydrate polymer materials are also within the spirit of the invention. E.g. the polymer material of the invention may comprise one or more polymers having substantially carbohydrate and/or especially cellulose or hemicellulose character. Also the polymer material may be composed of cellulose or hemicellulose that have been modified by way of substitution or addition. Both natural and synthetic polymers can be used within the scope of the invention. The polymer material may be crystalline, or in a disordered, amorphous form, or a mixture of the two.

In one embodiment of the present invention, the ratio of the inner diameter to the outer diameter of the polymer shells is variable from 40 to 90%, and preferably from 50 to 70%, as a result of variable salt concentration or variable pH or over time.

The shell according to the invention displays an outer diameter of between 0.1 µm and 10 mm, but diameters ranging from 0.1 µm to 10 µm, from 10 µm to 50 µm, from 50 µm to 100 µm, from 100 µm to 500 µm, from 500 µm to 1 mm, and from 1 mm to 10 mm, are all within the scope of the invention, depending on the purpose and on the field of application of the polymer shells. In yet another embodiment of the present invention, the inner diameter of the shell is between 0.5 mm and 6 mm, but the inner diameters may also range from 0.1 µm to 10 µm, from 10 µm to 50 µm, from 50 µm to 100 µm, from 100 µm to 500 µm, from 500 µm to 1 mm, and from 1 mm to 10 mm, again depending on the purpose and on the field of application.

Figure 13:
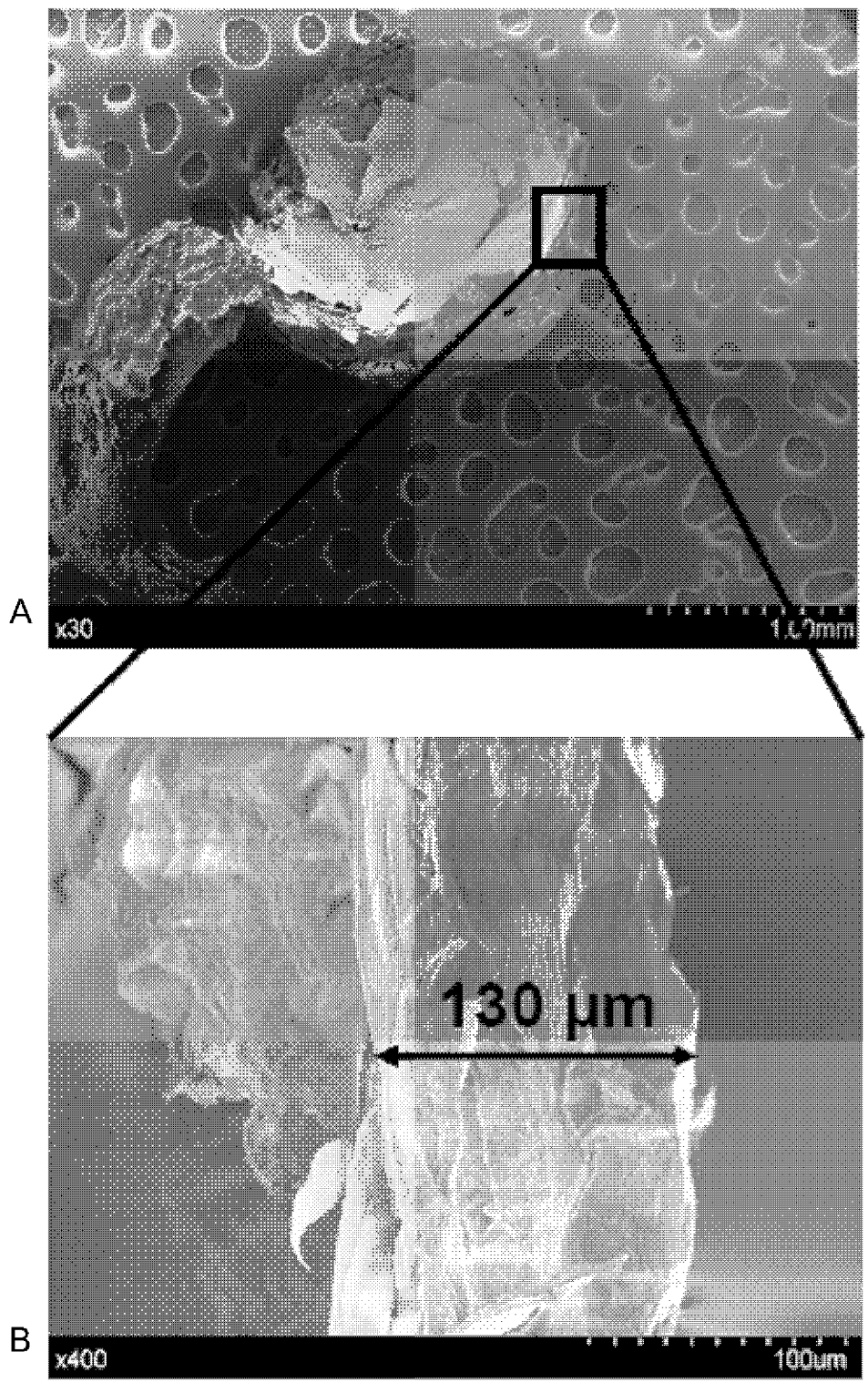
Figure 14:
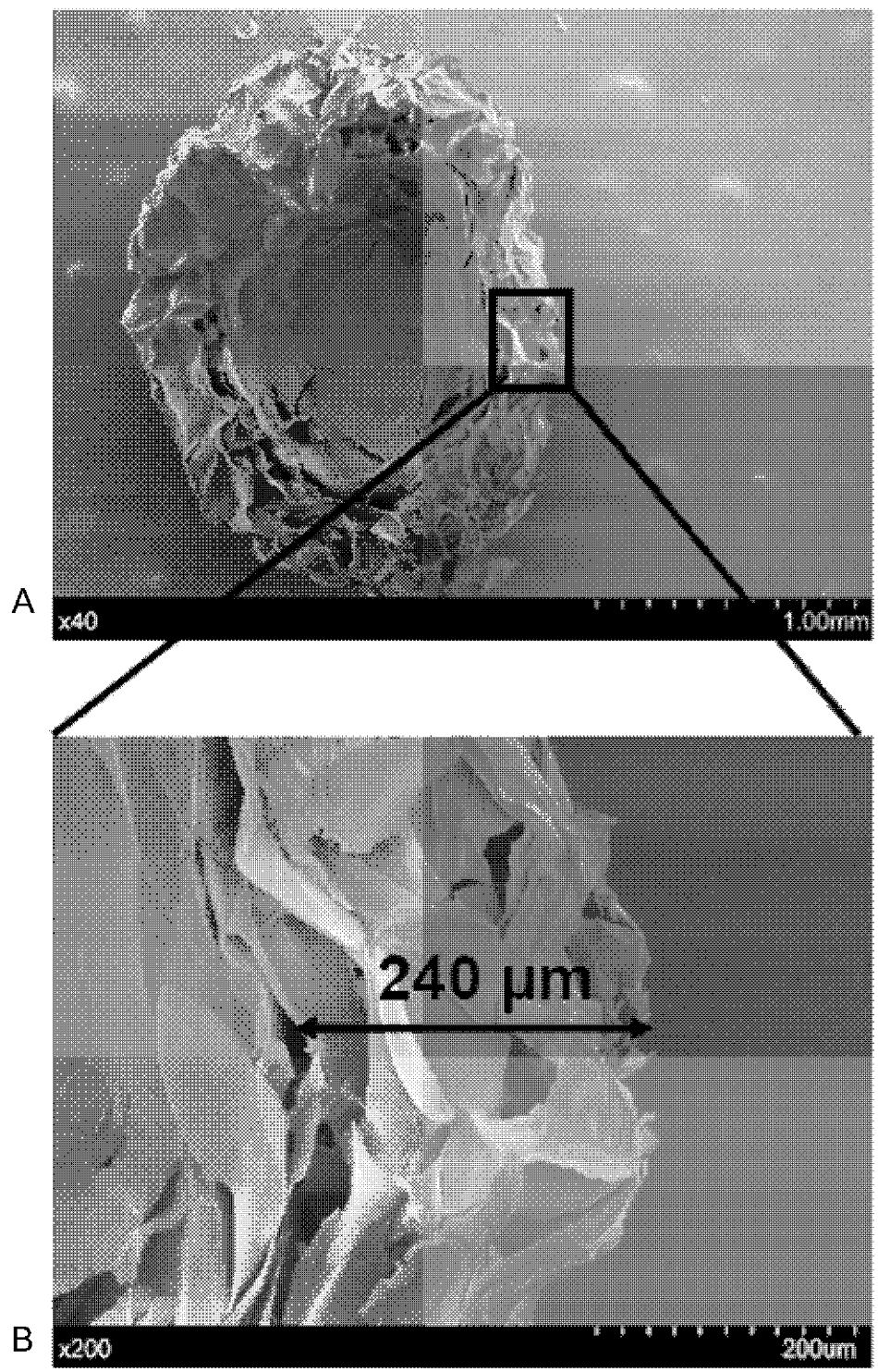
Figure 15:
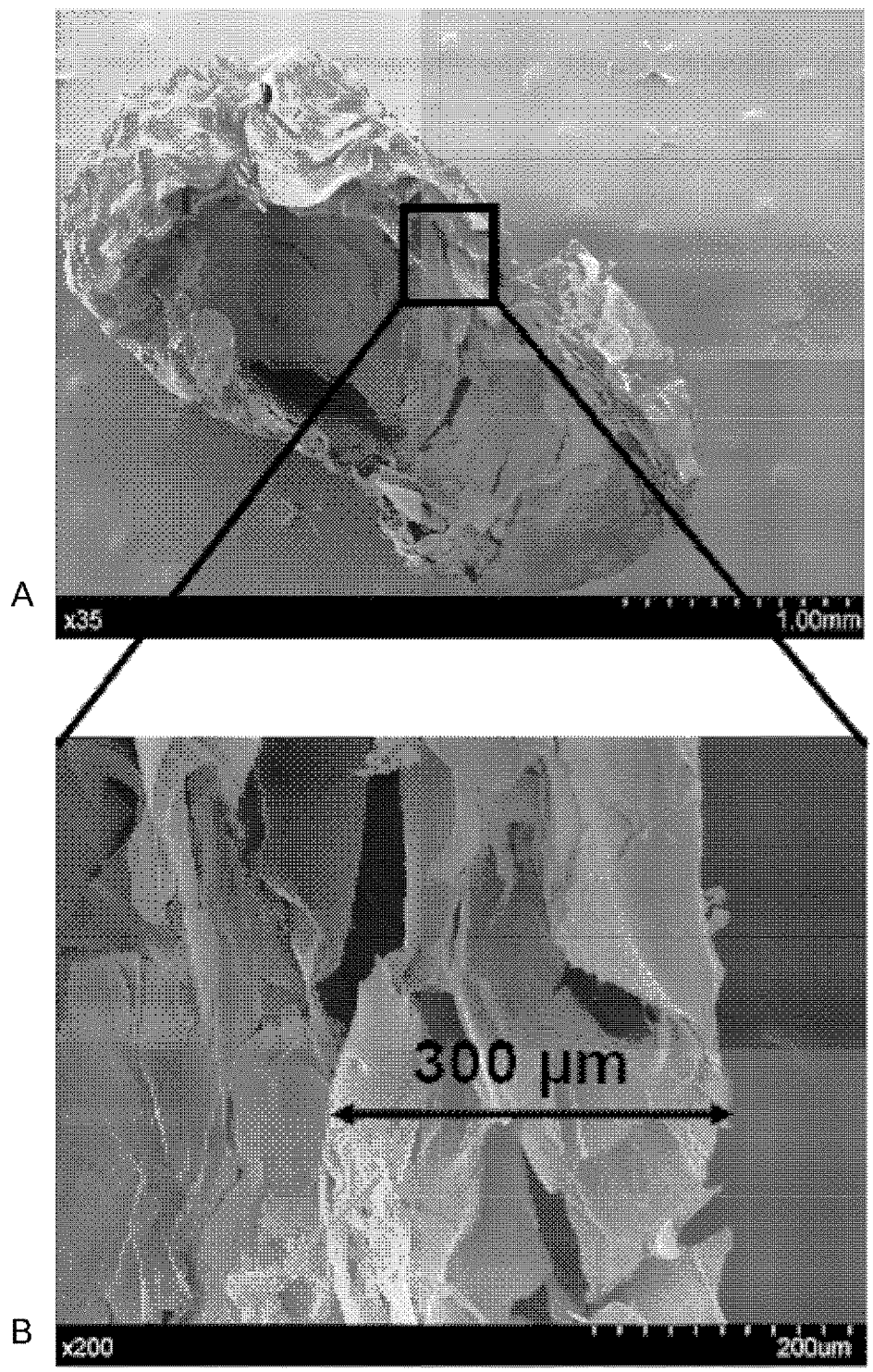
Figure 16:
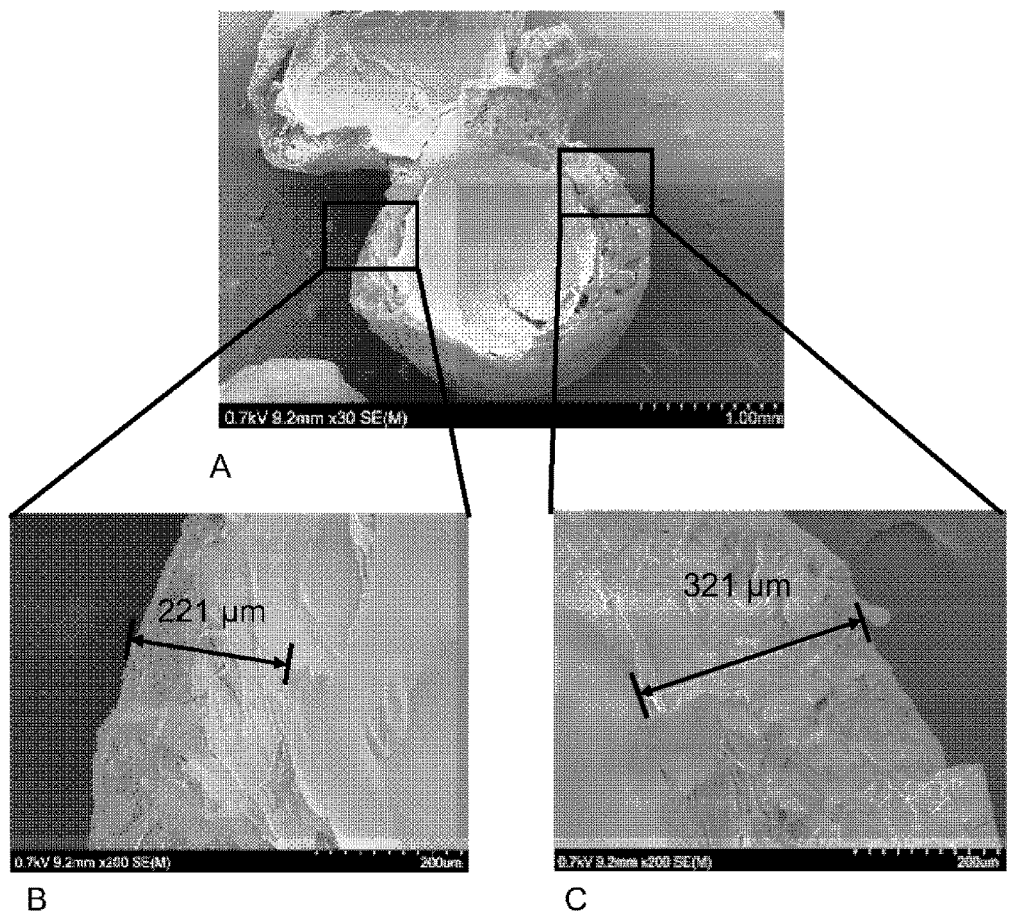
Figure 17:
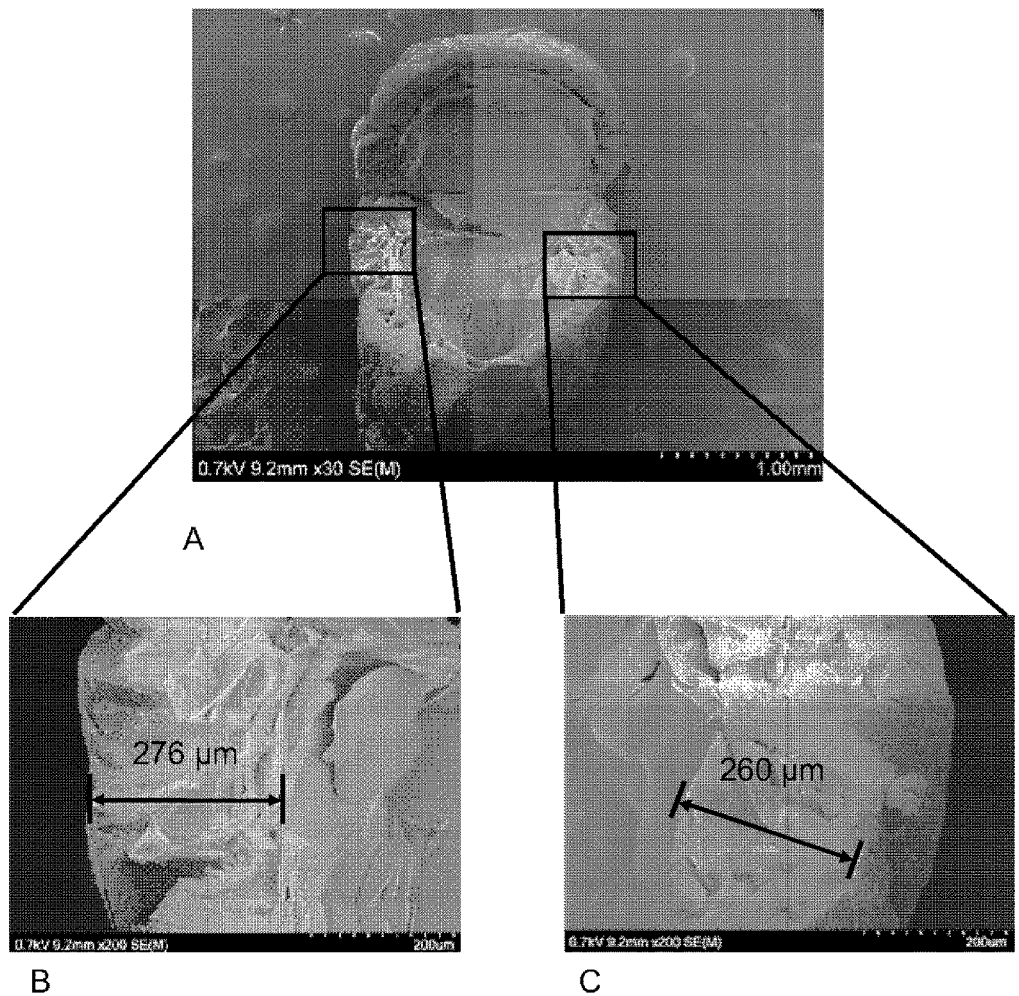
Figure 18:
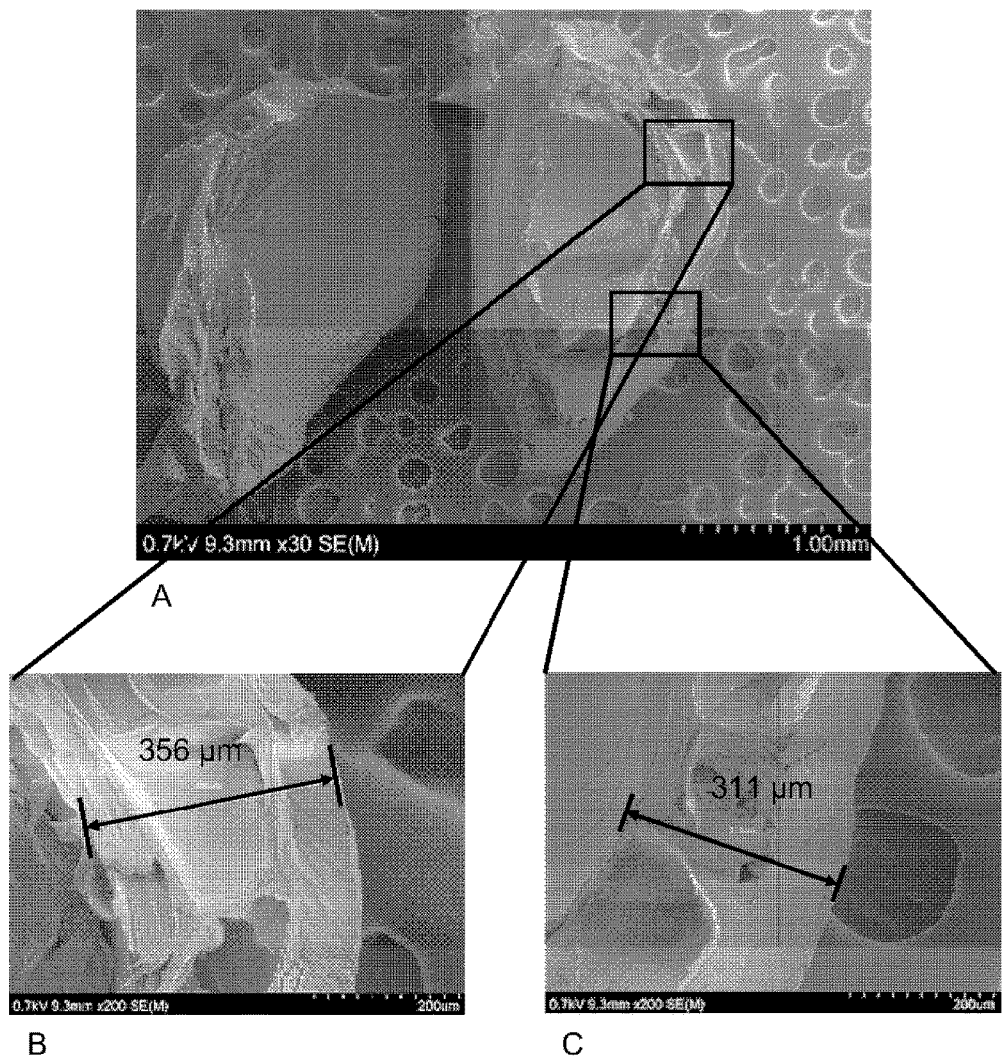
Figure 19:
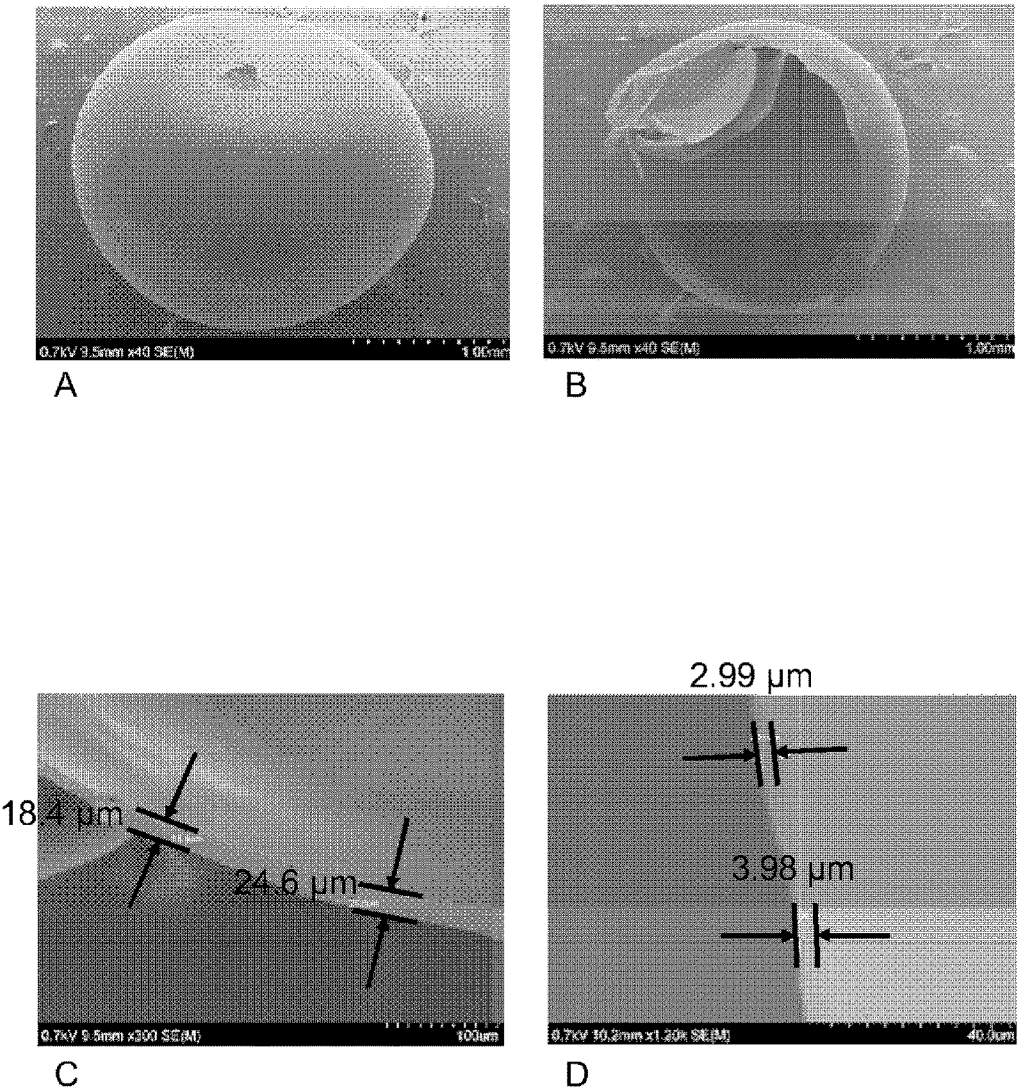

As can be seen from FIGS. 13 and 16, polymer shells comprising 1% cellulose may exhibit a shell wall thickness ranging from approximately 100 µm to 300 µm. Shells with a cellulose content of 1.5% may display slightly thicker shell walls, ranging from approximately 200 µm to 300 µm, as can be seen from FIGS. 14, 15, and 17. Shells with a cellulose content of 2% may have even thicker shell walls, with FIG. 18 showing a cellulose polymer shell having a shell wall thickness of approximately 350 µm. Certain cellulose shells, for instance shells that are exposed to microwave drying after formation, exhibit significantly less thick shell walls, as can be seen from FIG. 19, with the thickness ranging from between approximately 2 µm to 30 µm. Thus, polymer shells having a shell wall thickness ranging from approximately 100 nm to 2 mm are within the scope of the invention. The shell wall thickness may preferably be in the interval between 0.5 µm and 500 µm, but other intervals may be desirable for specific applications.

According to the invention, washed polymer shells, insoluble in polar solvents, exhibit different characteristics than unwashed shells. The influence of external factors on the shells is affected by the metal ion salt or the alkali metal ion salt, for instance LiCl, associated with the unwashed shells. Further according to the present invention, the degree of substitution of the polymer comprising the washed shells influences the thickness of the walls and the swelling of the shells, with a higher degree of substitution resulting in thicker walls and a smaller outer diameter, indicating increased swelling of the polymer. The reason for this is that the increasing charge of the polymer results in a larger difference in chemical potential which is compensated for by dilution (swelling) of the material. Consequently according to one embodiment of the present invention, the polymer material with the highest degree of substitution comprising the washed polymer shells, insoluble in polar solvents, display a higher degree of swelling when increasing the salt concentration or increasing the pH. However, in another embodiment a decreasing salt concentration results in a higher degree of swelling.

In another embodiment of the present invention, the surface of the polymer shell has been modified to attain certain desired properties. Modifying the surface of the shell may comprise attaching functional and/or active groups, either covalently or through electrostatic or hydrophobic forces or through any other means of attachment known to a person skilled in the art. The modifications may comprise atoms, molecules, macromolecules, polymers, aggregates, particles, fibres, fibrils and other components known to the skilled person. In yet another embodiment, additional polymers with properties suitable for drug delivery or chromatography applications are attached to the polymer shells. Such polymers can for instance include non-carbohydrate and carbohydrate polymers such as chitosan, but proteins, polypeptides, and oligonucleotides may also be attached to the polymer shells. The attachment can rely on either covalent or non-covalent bonds and furthermore comprise more than one additional polymer or oligomer.

In one preferred embodiment, the additional polymer that is used to modify the surface of the polymer shell is a water soluble carbohydrate. This water soluble carbohydrate may be modified before or after the modification of the surface of polymer shell. The modified water soluble carbohydrate can be xyloglucan. The modification of xyloglucan can be done according the invention by Brumer and co-workers EP1448840B1 where a chemo-enzymatic method utilizing the enzyme xyloglucan endotransglycosylase is used for the modification of cellulose. Another method for the modification of xyloglucan is disclosed by Slättegård and co-workers (U.S. provisional No. 61/150,021) where the xyloglucan is aminated, by a reductive amination procedure. An aminated xyloglucan molecule can be used for linking antibodies, proteins or peptides as disclosed in WO2008/104528 or adding chemical compound conferring the sealing properties or other compatibilities.

In this embodiment, the modified xyloglucan is attached to the polymer shells in order to confer properties suitable for drug delivery or chromatography applications or any other desirable property, such as reversible sealing of the shell. According to the invention, an additional embodiment may comprise reversible sealing of the shell using either a suitable polymer, for instance chitosan, or a chemical compound, comprising for instance $CaCO_3$, exhibiting different properties upon exposure to variable surrounding conditions, such as pH and salt concentration. Reversible sealing can e.g. be obtained by immersing the polymer shell in a solution of a suitable polymer or chemical compound conferring the sealing properties. Gelatine is widely used in drug delivery applications, since gelatine is digested by enzymes in the gastrointestinal system, leading to release of the drug. The reversible sealing properties may e.g. be used in drug delivery applications, in order to control release of the contents of the polymer shell. Removal of the sealing properties may be achieved through exposure to altered pH, salt concentration, or temperature. Polymer shells produced with $CaCO_3$ exhibit a significantly slower release of compounds encased within the shell, implying that incorporation the number of pores in the shell has been reduced, or that the pore size is decreased. Undissolved $CaCO_3$ is surmised to cover the pores, thereby reducing the diffusivity and permeability of the polymer shells.

One embodiment of the invention relates to polymer shells substantially comprising carbohydrate polymers produced by the method of the present invention.

In another embodiment of the present invention, a drug delivery device comprising the polymer shell is described. The drug delivery device may comprise a vehicle for, for instance, per os (p. o.), intravenous (i. v.), intra-peritoneal (i. p.), intracerebro-ventricular (i. c. v.), intramuscular (i. m.), intranasal, and/or intrathecal delivery of small-molecule, macromolecule, and/or biopharmaceutical drugs, or a vehicle for a vaccine and/or a non-specific immune response enhancer, or other pharmaceutically interesting compounds known to a person skilled in the art. Further, the drug delivery device could be utilized for local delivery of pharmaceutically interesting compounds or for sustained delivery over a longer period of time. In a further embodiment, the drug or the pharmaceutical composition to be included in the vehicle acts as the core-forming substance aiding formation of the polymer shell and thereby being incorporated into the drug delivery vehicle. Alternatively, the drug can be dissolved in the second polar solution for incorporation into the vehicle upon precipitation of the polymer shell, for instance through preferential co-precipitation together with the polymer or through some other form of unspecific or specific chemical interaction. In yet another embodiment of the present invention, the polymer shell is loaded with a drug of interest after its formation, for instance through exploiting the responsive properties of the polymer shell.

In an additional embodiment of the invention, the polymer shell is employed as a means for chromatographic separation, wherein the shell acts as a solid phase component, for instance as a stationary phase on a column for liquid chromatography (LC), comprising for example high-performance liquid chromatography (HPLC), size exclusion chromatography (SEC), ion exchange chromatography, affinity chromatography, immobilized metal affinity chromatography (IMAC), or hydrophobicity chromatography, reverse-phase (RPC) chromatography, thin layer chromatography (TLC) and/or gas chromatography, further comprising techniques known to a person skilled in the art, for both preparative and analytical purposes.

Further, the polymer shells Filling may be utilized as filling material for various purposes, inter alia insulation, packaging material, joint filling material, and/or weathering material.

EXAMPLES

Materials and Methods a. Cellulose Polymers

Three types of cellulose were investigated by the inventors in the present experiments. Two dissolving pulps with varying degree of substitution (D. S.) (0.0065 and 0.015) were utilized, as well as a bleached chemical sulphate long-fibre pulp known as Grycksbo.

b. Light Microscopy

The present inventors utilized light microscopy to evaluate the dimensions of the polymer shells, insoluble in said polar solvent. Using a Carl Zeiss Stemi SV8, the influence of salt concentration and pH on the outer and the inner diameters of the polymer shells could be determined, and the presence of a space inside the shell was also detected.

c. Confocal Microscopy

The inventors aimed at utilizing confocal microscopy, but as a result of the thickness of the walls of the shells the optical sections did not penetrate the shells to a sufficient degree, making it difficult to carry out any measurements.

d. Spectrophotometry

In order to simulate drug release from the polymer shells, the release of a commonly utilized dye incorporated into the shells was measured spectrophotometrically, through repeated sampling of an aqueous solution containing said shells.

Example 1: Effects Mediated by Variable pH Over Time

Figure 1:
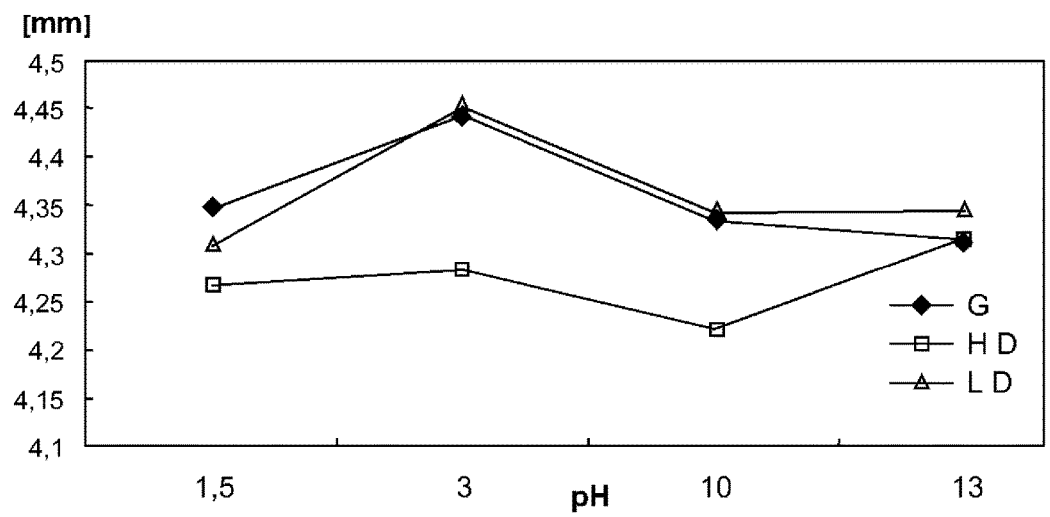
FIG. 1 shows an initial measurement of the total diameter of polymer shells over a pH interval ranging from 1.5 to 13. X-axis: pH, Y-axis: Total diameter [mm], G=Grycksbo, H D=High Ds, L D=Low Ds FIG. 2 displays a later measurement of the total diameter of polymer shells over a pH interval ranging from 1.5 to 13. X-axis: pH, Y-axis: Total diameter [mm], G=Grycksbo, H D=High Ds, L D=Low Ds
Figure 2:
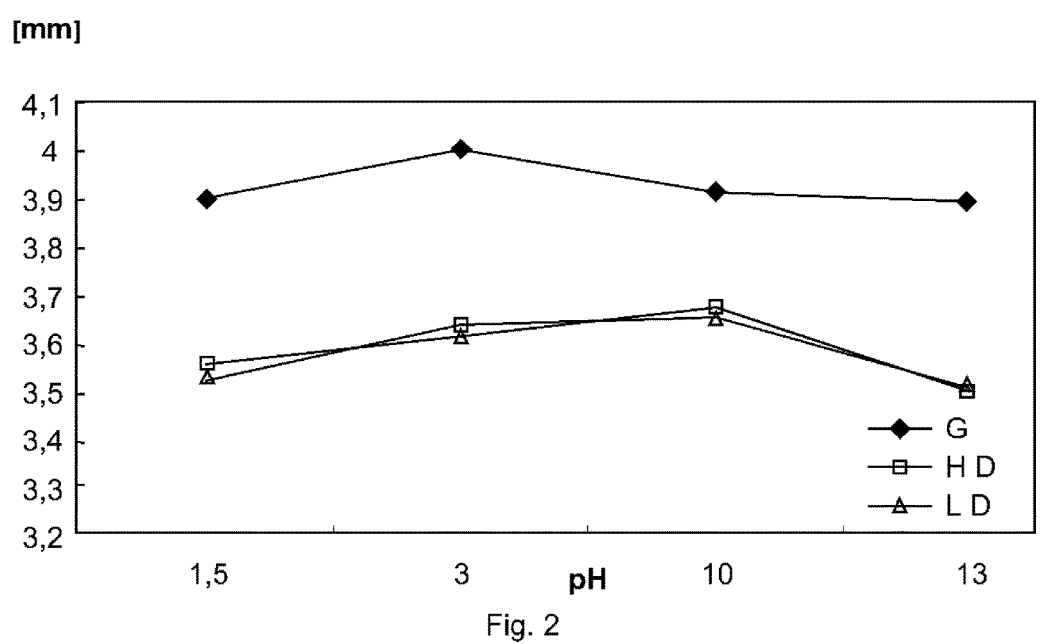

As can be seen in Table 1 to Table 3, and FIG. 1, the initial outer diameter of the shells increased slightly at higher pH. Comparing the outer diameters in FIG. 1 with the outer diameters in FIG. 2, as well as the initial values and the values after 2 to 3 hours, it is clear that all three polymer types decreased in size and that there was a high degree of similarity between the two dissolving pulps. An explanation could possible be derived from a decreased gas pressure inside the shell upon water diffusing into it, decreasing the outward radial pressure and thereby decreasing the size of the shell.

TABLE 1

Pulp type: Grycksbo 400

| | Total diameter (mm) | | Total wall thickness (mm) in one dimension | |
|---|---|---|---|---|
| pH | Initial value | Later value | Initial value | Later value |
| 1.5 | 4.35 | 3.90 | 1.99 | 1.58 |
| 3.0 | 4.44 | 4.00 | 2.13 | 1.71 |
| 10.0 | 4.34 | 3.91 | 2.05 | 1.73 |
| 13.0 | 4.31 | 3.89 | 2.61 | 1.97 |

TABLE 2

Pulp type: Dissolving High Ds

| | Total diameter (mm) | | Total wall thickness (mm) in one dimension | |
|---|---|---|---|---|
| pH | Initial value | Later value | Initial value | Later value |
| 1.5 | 4.27 | 3.55 | 1.50 | 1.12 |
| 3.0 | 4.28 | 3.61 | 1.68 | 1.29 |
| 10.0 | 4.22 | 3.67 | 1.85 | 1.55 |
| 13.0 | 4.32 | 3.49 | 2.37 | 1.64 |

TABLE 3

Pulp type: Dissolving low Ds

| | Total diameter (mm) | | Total wall thickness (mm) in one dimension | |
|---|---|---|---|---|
| pH | Initial value | Later value | Initial value | Later value |
| 1.5 | 4.31 | 3.52 | 1.46 | 1.17 |
| 3.0 | 4.45 | 3.63 | 1.70 | 1.26 |
| 10.0 | 4.34 | 3.65 | 2.01 | 1.42 |
| 13.0 | 4.35 | 3.50 | 2.57 | 1.69 |

Figure 3:
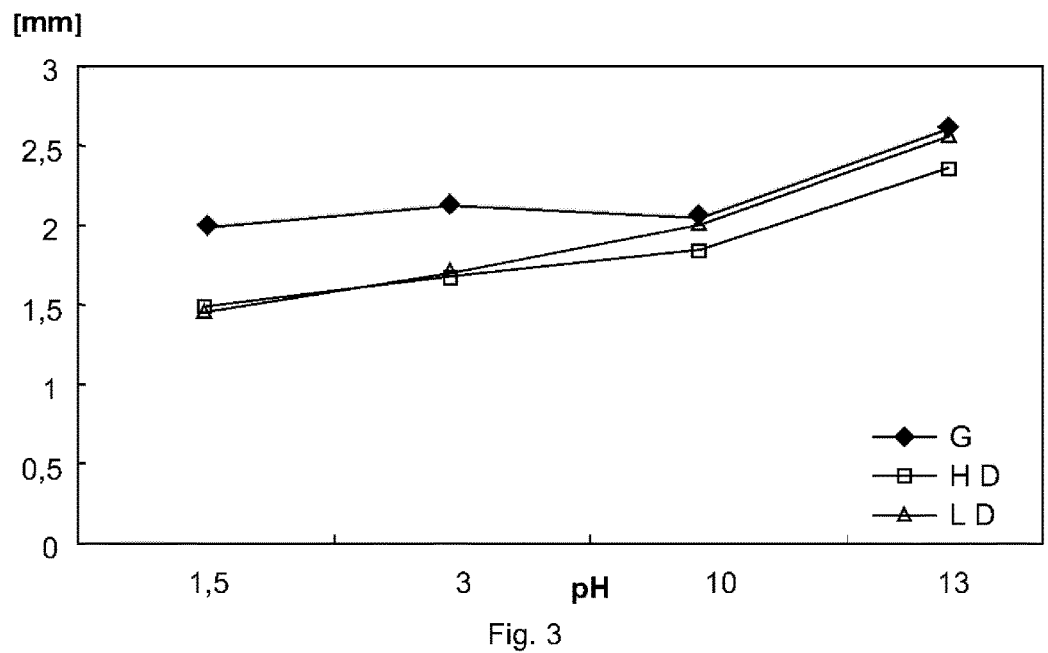
FIG. 3 shows an initial measurement of the wall thickness of polymer shells over a pH interval ranging from 1.5 to 13. X-axis: pH, Y-axis: Wall thickness [mm], G=Grycksbo, H D=High Ds, L D=Low Ds
Figure 4:
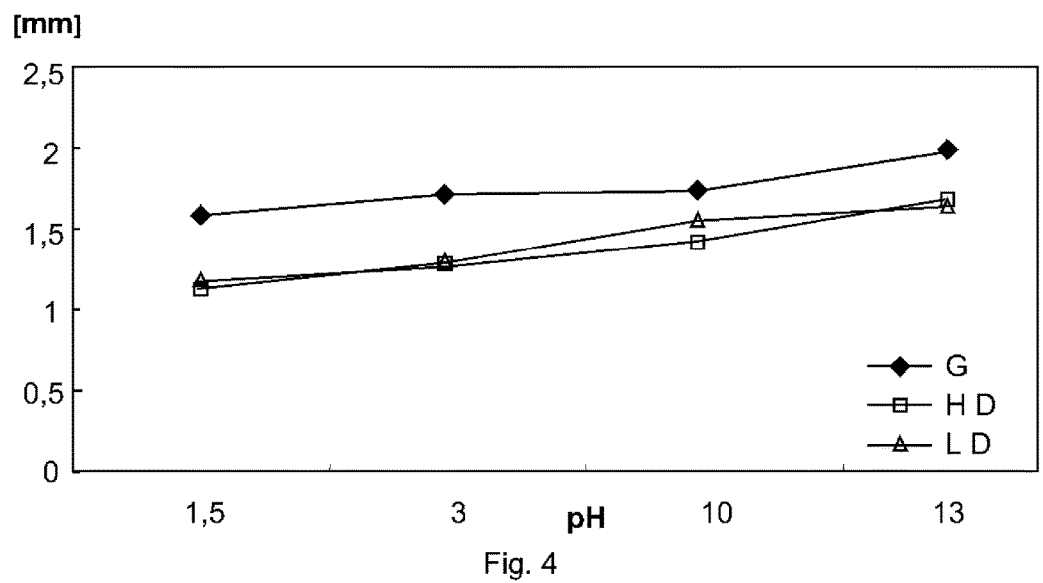
FIG. 4 shows a later measurement of the wall thickness of polymer shells over a pH interval ranging from 1.5 to 13. X-axis: pH, Y-axis: Wall thickness [mm]

From the initial thickness of the walls of the shells presented in FIG. 3, it is clear that the thickness increased with increasing pH. The increase over the pH range of 1.5 to 13 was between 0.6 to 11 mm depending on the cellulose pulp used. The space inside the shells was affected by the pH and the largest volume was detected at low pH, as a result of increased swelling with increasing pH. When the charged groups on the cellulose, primarily the carboxylic groups, were ionized at higher pH, the difference in chemical potential between the charged cellulose and the aqueous solution resulted in an influx of water into the cellulose, leading to increased swelling. A similar trend can be seen in FIG. 4, where the solution was left for a few hours. However, the difference in thickness of the walls of the shells was here between 0.4 and 0.5 mm over a pH range of 1.5 to 13.

Radial inwards expansion of the shells was observed upon raising the pH, resulting in increased wall thickness and consequently decreased volume of the space inside the shell. One potential explanation for this behaviour could be that the when alkaline water enters the shell, gaseous carbon dioxide becomes increasingly soluble, resulting in diffusion of the solubilised $CO_2$ out from the shell. The gas pressure is consequently reduced, allowing the walls to expand inwards and the volume of the space inside shell to decrease. The rationale behind this explanation derives from the fact that virtually no difference can be detected between the two dissolving pulps, in spite of their different charges, and the fact that no substantial change in outer diameter is detected upon varying pH. If the swelling primarily was a result of the charged groups on the cellulose, a more significant difference between the two dissolving pulps would have been detected. It is noteworthy that these tests were not carried out on washed shells, implying the presence of a certain amount of LiCl ions, which affects the swelling properties and partially explains why the difference between the two dissolving pulps is rather low.

Example 2: Effects Mediated by Variable Salt Concentration Over Time

The salt concentration was varied over a concentration ranging from 0 to 0.1 M. The initial values were measured using light microscopy at an initial time point and after 2 to 3 hours.

Figure 5:
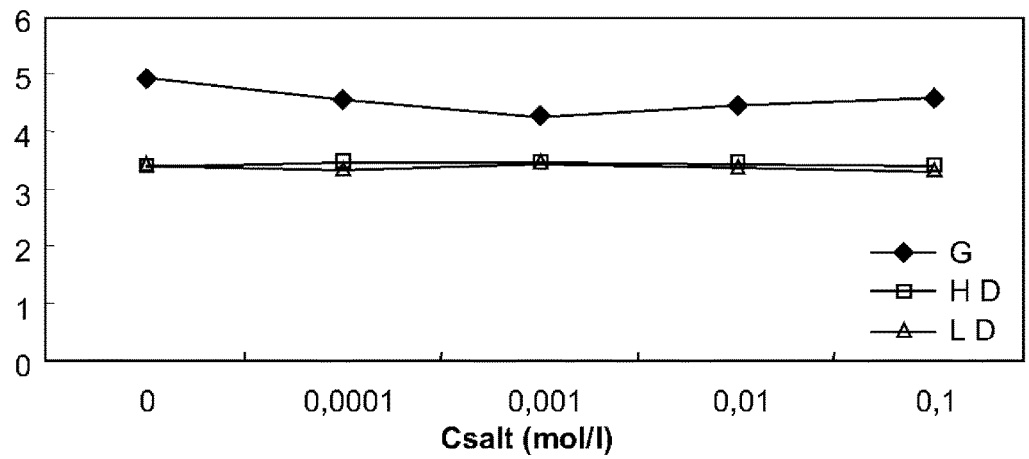
FIG. 5 displays an initial measurement of the total diameter of polymer shells over a salt concentration interval ranging from 0 to 0.1 mol/l. X-axis: Conc. of salt [mol/l], Y-axis: Total diameter [mm]

The obtained results indicate that the outer diameter did not change significantly for the two dissolving pulps when altering the salt concentration, but the shell comprised of sulphate pulp increased in size. The explanation for this relates to a high degree of deformation of the normally substantially spherical shells, leading to an increased diameter with the applied two-dimensional measurement. Consequently, the error was too large for the Grycksbo pulp, but one could conclude that the two dissolving pulps displayed highly similar characteristics (FIG. 5).

Figure 6:
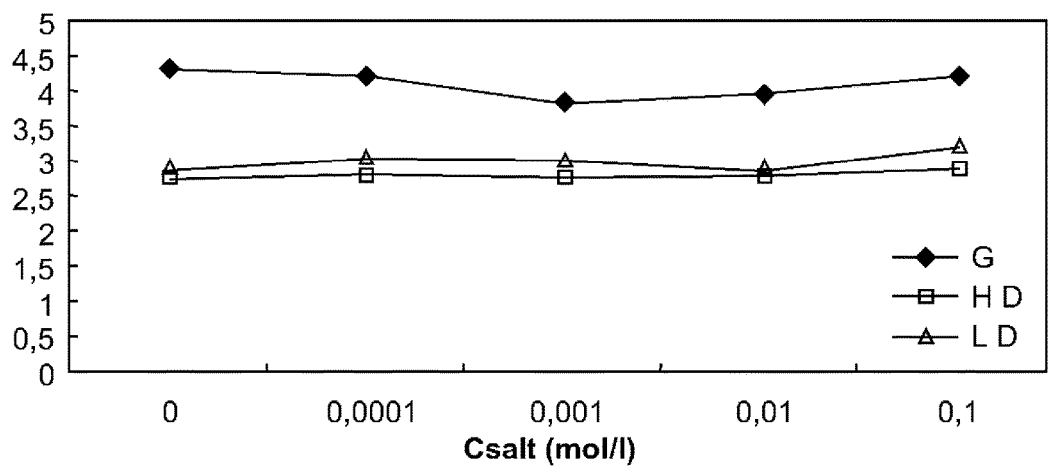
FIG. 6 shows a later measurement of the total diameter of polymer shells over a salt concentration interval ranging from 0 to 0.1 mol/l. X-axis: Conc. of salt [mol/l], Y-axis: Total diameter [mm]
Figure 7:
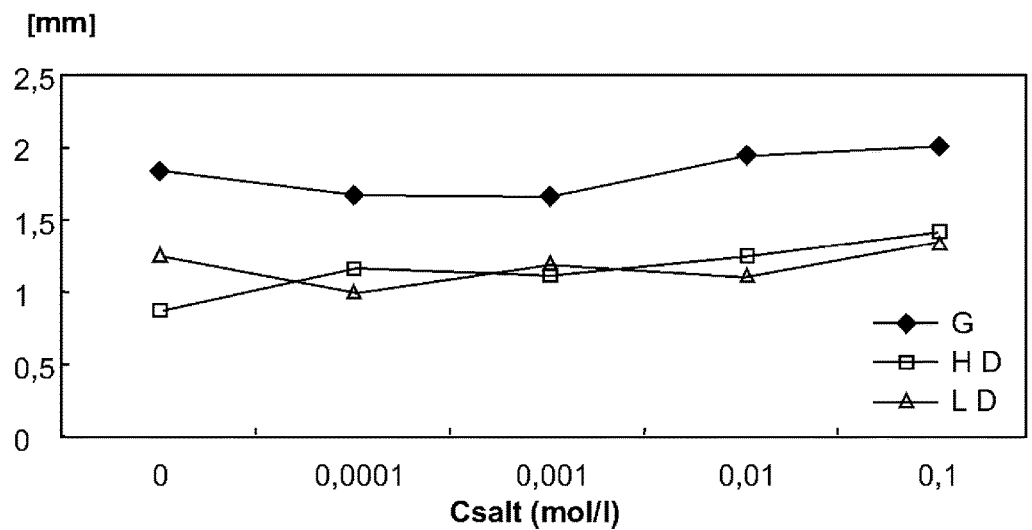
FIG. 7 displays an initial measurement of the total wall thickness in one dimension of polymer shells over a salt concentration interval ranging from 0 to 0.1 mol/l. X-axis: Conc. of salt [mol/l], Y-axis: Wall thickness [mm]

After 2 to 3 hours in solution over a range of different salt concentrations, the dissolving pulp with the lowest D. S. had a slightly larger outer diameter than the dissolving pulp with higher D. S, whereas the sulphate pulp displayed the largest diameter (FIG. 6), for the abovementioned reason. After a few hours in solution, the outer diameter and the thickness of the walls decreased overall, compare FIG. 5 and FIG. 6. Furthermore, with increasing salt concentration the thickness of the walls as well as the outer diameter increased for the two dissolving pulps, resulting in a smaller volume of the space inside the shell (FIG. 7 and Table 5 to Table 7).

TABLE 4

Pulp type: Grycksbo 400

| | Total diameter (mm) | | Total wall thickness (mm) in one dimension | |
|---|---|---|---|---|
| Csalt | Initial value | Later value | Initial value | Later value |
| 0 | 4.90 | 4.30 | 1.82 | 1.57 |
| 0.0001 | 4.53 | 4.22 | 1.66 | 0.93 |
| 0.001 | 4.24 | 3.81 | 1.64 | 1.36 |
| 0.01 | 4.44 | 3.97 | 1.92 | 1.56 |
| 0.1 | 4.55 | 4.21 | 1.99 | 1.53 |

TABLE 5

Pulp type: Dissolving High Ds

| | Total diameter (mm) | | Total wall thickness (mm) in one dimension | |
|---|---|---|---|---|
| Csalt | Initial value | Later value | Initial value | Later value |
| 0.0001 | 3.44 | 2.81 | 1.15 | 0.70 |
| 0.001 | 3.46 | 2.75 | 1.10 | 0.84 |
| 0.01 | 3.42 | 2.78 | 1.23 | 0.74 |
| 0.1 | 3.39 | 2.90 | 1.40 | 0.87 |

TABLE 6

Pulp type: Dissolving low Ds

| | Total diameter (mm) | | Total wall thickness (mm) in one dimension | |
|---|---|---|---|---|
| Csalt | Initial value | Later value | Initial value | Later value |
| 0 | 3.39 | 2.88 | 1.22 | 0.54 |
| 0.0001 | 3.31 | 3.02 | 0.98 | 0.64 |

TABLE 6-continued

Pulp type: Dissolving low Ds

| | Total diameter (mm) | | Total wall thickness (mm) in one dimension | |
|---|---|---|---|---|
| Csalt | Initial value | Later value | Initial value | Later value |
| 0.001 | 3.43 | 3.01 | 1.17 | 0.78 |
| 0.01 | 3.36 | 2.84 | 1.09 | 0.56 |
| 0.1 | 3.27 | 3.20 | 1.34 | 0.73 |

Example 3: Influence of Washing on the Properties of the Cellulose Shells

Table 7 to table 9 show the change in the sizes of the shells after washing. In accordance with the previous results, the outer diameters of the shells do not change significantly when changing neither the pH nor the salt concentration. However, the thickness of the walls of the shell increased, indicating an inwards radial swelling when ions were added to the solution, implying that the forces restraining the swelling were reduced when raising the pH to 10 or increasing the salt concentration to $10^{-3}$ M.

TABLE 7

Pulp type: Grycksbo 400

| Before treatment (pH 6.5, Csalt = 0) | | | | After treatment | | |
|---|---|---|---|---|---|---|
| Total diameter | Diameter hollow space | Total wall thickness | Type | Total diameter | Diameter hollow space | Total wall thickness |
| 3.93 | 2.69 | 1.24 | pH = 10 | 3.92 | 2.54 | 1.37 |
| 3.83 | 2.59 | 1.24 | Csalt = 0.001 | 3.86 | 2.47 | 1.39 |

TABLE 8

Pulp type: Dissolving High Ds

| Before treatment (pH 6.5, Csalt = 0) | | | | After treatment | | |
|---|---|---|---|---|---|---|
| Total diameter | Diameter hollow space | Total wall thickness | Type | Total diameter | Diameter hollow space | Total wall thickness |
| 3.49 | 2.29 | 1.2 | pH = 10 | 3.51 | 2.22 | 1.3 |
| 3.54 | 2.35 | 1.2 | Csalt = 0.001 | 3.56 | 2.25 | 1.32 |

TABLE 9

Pulp type: Dissolving low Ds

| Before treatment (pH 6.5, Csalt = 0) | | | | After treatment | | |
|---|---|---|---|---|---|---|
| Total diameter | Diameter hollow space | Total wall thickness | Type | Total diameter | Diameter hollow space | Total wall thickness |
| 3.7 | 2.65 | 1.05 | pH = 10 | 3.78 | 2.54 | 1.23 |
| 3.85 | 2.68 | 1.16 | Csalt = 0.001 | 3.68 | 2.47 | 1.2 |

Comparing the two dissolving pulps, one realizes that the pulp with the highest D. S. possesses the highest thickness of the walls as well as smaller outer diameter. Consequently, the swelling of the dissolving pulp with the highest D. S. was larger than the swelling of the dissolving pulp with lower D. S., an implication of the fact that the cellulose with the highest charge induces a bigger difference in chemical potential, which is compensated for by swelling (dilution).

Example 4: Dye Release Experiments

In order to simulate the release of a substance from the polymer shells, a coloured compound (methyl orange) was absorbed to the shells. Initially, 1.5% w/w dissolving pulp was dissolved in LiCl/DMAC, either in the presence or in the absence of $CaCO_3$ and the cellulose shells were precipitated as previously described. Methyl orange was subsequently absorbed to the shells followed by transfer of the shells to a water bath. Samples were taken from the water bath and the absorbance at 470 nm was measured spectrophotometrically.

Figure 8:
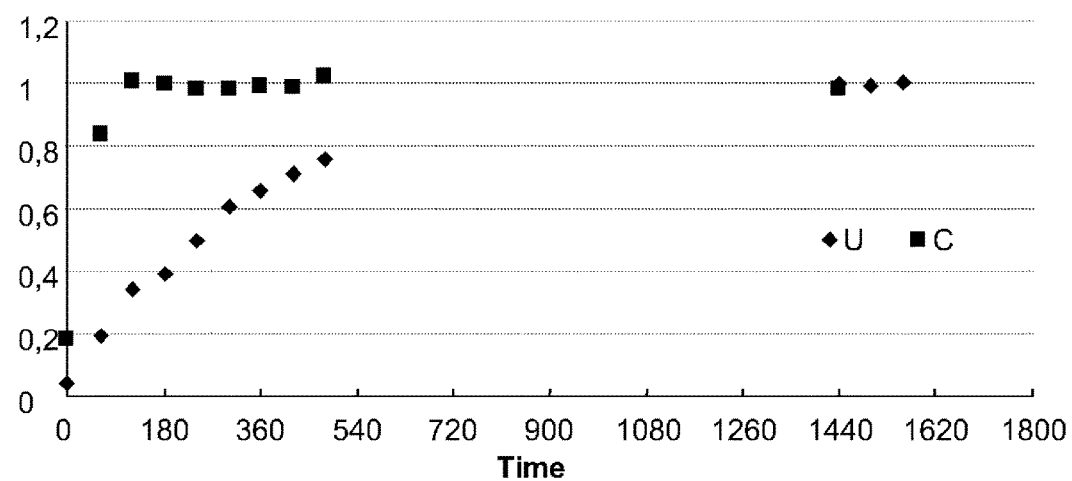
FIG. 8 shows a simulated drug release experiment, plotting the release of dye over time at pH 2 in deionized water (concentration outside the beads). X-axis: Time in minutes Y-axis: Normalized concentration U=Untreated, C=$CaCO_3$ FIG. 9 portrays microfluidic reaction chambers that may be utilized for the present invention.

Samples were, during the first eight hours, taken every hour but measurements after 24 hours indicated that the dye incorporated into the shells formed in the presence of $CaCO_3$ diffuses more rapidly than the dye in the shells formed in the absence of $CaCO_3$ (FIG. 8). After eight hours, the dye in the shells formed in the presence of $CaCO_3$ was essentially completely released from the shells, whereas the equilibrium state was reached later for the untreated shells. The faster release of methyl orange from the shells formed in the presence of $CaCO_3$ (FIG. 8) can be explained based on the increased solubility of $CaCO_3$ at lower pH. Upon shells formation, the $CaCO_3$ incorporated into the shells will solubilise, resulting in the formation of pores facilitating dye release from the carbohydrate polymer shells. The plot of normalized dye concentration versus time (FIG. 8) indicates that a sustained release is achievable for over two hours when including $CaCO_3$ in the formulation of the shells, and that the absence of $CaCO_3$ in the formulation generates shells with even longer sustained release properties.

Example 5: Microfluidic Polymer Shell Production

The initial stage of the microfluidic polymer shell production (for instance in accordance with FIG. 9) pertained to generation of monodisperse water droplets, with a size of 60 µm, in polydimethylsiloxane (PDMS), through flowing water as an inner fluid and PDMS oil as an outer fluid. The monodisperse water droplets surrounded by PDMS were transported through a round glass capillary and in the end of the tube a cellulose/LiCl/DMAc-solution was introduced. As a result of the flow dynamics, the cellulose solution covered the PDMS and the water, producing a double emulsion. The PDMS oil functioned as an inert protecting agent, delaying the normally very fast interaction between cellulose and water. This unique set-up prevented clogging, which is one of the major drawbacks when using microfluidics as a media for solidifications of cellulose. Once a device was clogged, it was usually rendered useless and a new one had to be built. Furthermore, by having PDMS oil surrounding the water droplets it was possible to introduce more shear stress which prevented early precipitated cellulose shells from sticking on the glass capillary. The geometry, presented in FIG. 19 below, with inner dimension starting from left; the square tubes have an inner width of 1 mm, the round glass tube had an inner diameter of 50 µm, the second opening of the same round capillary had an inner diameter of 180 µm, the collection tube had an opening of 400 µm. The dotted coloured arrows signify inlets where the fluids are introduced into the microfluidic device. The non-dotted coloured arrows represent flow direction of fluids inside the microfluidic device. The size of the hollow cellulose shells produced using microfluidics is reduced from millimeter to micrometer. The most important parameter determining the sizes of the shells produced by the microfluidic technology is the size of the glass tapers (see FIG. 5 or FIG. 19), the exit capillary size of the glass tube of the water inlet. The bigger the taper, the bigger the cellulose shells.

Example 6: Drying of Polymer Shells

The sizes of wet hollow cellulose shells were measured using microscopy prior to air-drying in ambient temperature. After five hours of air-drying, the sizes were measured again. The diameter of the cellulose shells decreased with a factor 2.6, i. e. more than 60%.

Cellulose shells prepared using LPG (60% propane and 40% butane) as the core-forming agent were dried in a domestic microwave oven (800 W) until totally dry (approximately 1.5 minutes). Unlike in the above example, the sizes of the shells did not decrease as a result of the drying, but the shells became hard. Upon releasing an applied physical pressure, the shells went back to their original shape and structure, virtually instantaneously. Furthermore, the shells became transparent upon visual inspection after having been microwave dried, potentially providing a highly interesting route to obtaining transparent shells for numerous applications.

Example 7: Emulsification Preparation 1 ml of hexane was dissolved in 5 ml of cellulose solution. The mixture is then shaken, creating an emulsion of hexane droplets in cellulose solution. This solution was then dripped into isopropanol whereby the droplets precipitates, creating a cellulose capsule filled with hexane.

Additionally, experiments were carried out where a third non-polar liquid (PDMS) was added before precipitating the cellulose. By adding PDMS as the third component in the mixture and then shaking the solution once more before the precipitation step in isopropanol, micro-sized shells were obtained.

Further, 2 ml of cellulose solution was fed with LPG and then transferred into a hexane solution. The mixture was then shaken and thereafter moved through a glass pipette into isopropanol where the cellulose shells precipitated and formed.

Example 8: Xyloglucan-FITC Modification of Cellulose Shells 10 mg of xyloglucan (XG), with a molecular weight of 4000 Da and labelled with fluorescein isothiocyanate (FITC), was added to 5 g of the DMAC-solution and stirred for about an hour until everything was dissolved. The solution was treated with $CO_2$ gas for 1 hour. Then the solution was dropped down in a water bath. The XG-FITC was adsorbed to the shells and the water in the water bath was analyzed in order to determine whether it contained any XG-FITC. Through addition of drops of water on a TLC plate followed by subsequent exposure to 360 nm UV irradiation, the interaction between the cellulose shells and the XG-FITC was assessed. No light was emitted from the TLC plate, confirming the absence of XG-FITC in the water solution.

Discussion

The outer diameter and the thickness of the walls of the shells are initially relatively large but decrease over time until equilibrium is reached. The volume of the space inside the shells is affected by pH and the largest volume is observed at low pH. The swelling of the shells occurs inwards in radial direction, the outer diameter remains relatively constant whereas the cellulose wall is expanding inwards upon exposure to variable salt concentrations and variable pH. For the washed shells, the dissolving pulp with the highest D. S. displayed a higher thickness of the walls of the shells than the dissolving pulp with lower D. S., implying that the pulp with the highest charge swells more when adding salt or increasing the pH. Additionally, the physical properties of the shells allow for sustained release of a model compound over a timeframe of several hours, and the release can furthermore be easily modulated, implying significant utility in drug delivery settings.

The ability to use microfluidic techniques for the preparation of the polymer shells is indicative of the high versatility and applicability of the present invention, providing various means for preparing shells of highly varying shapes and sizes. Further, the differential effects exerted by different drying conditions imply that yet another parameter can be utilized to control the physical characteristics of the polymer shells. Additionally, surface modification is another important tool for tailoring the properties of the polymer shells, either through the use of salts, small molecules, and/or polymers of various origins.

The invention claimed is:

1. A method for preparing polymer shells, comprising the steps of:
   (a) dissolving a polymer component in a first solvent;
   (b) dissolving a core-forming substance in the solution obtained in step (a), wherein the core-forming substance comprises at least one gas, and wherein said dissolving comprises feeding said gas into the solution obtained in step (a) or pressurizing the solution obtained in step (a) with said gas, thereby dissolving the gas in the solution; and
   (c) precipitating the polymer component and simultaneously forming cores from the core-forming substance by contacting the solution of step (b) with a second solution by transferring the solution of step (b) to the second solution by dripping or spraying, wherein droplets of the solution of step (b) are formed prior to contacting the second solution, wherein the second solution comprises a second solvent of a polar character and a surfactant, and wherein the polymer component is insoluble in the second solvent, thereby forming precipitated polymer shells having an outer diameter of from about 10 µm to about 10 mm around said cores when the solution obtained in step (b) is entering the second solution; and
   wherein the polymer shells are substantially spherical.

2. The method according to claim 1, characterized in that said polymer component consists essentially of a polymer selected from the group consisting of cellulose, hemicellulose, chitosan, galactoglucomannan, and derivatives thereof.

3. The method according to claim 1, wherein the first solvent is dimethylacetamide (DMAc) or N-methyl morpholine oxide (NMMO).

4. The method according to claim 1, wherein the second solvent is an aqueous solvent or a polar solvent.

5. The method according to claim 1, wherein the solution of step (b) is transferred to the second solution with a spray device.

6. A method for preparing polymer shells, comprising the steps of:
   (a) dissolving a polymer component in a first solvent, wherein the polymer component is selected from the group consisting of cellulose, hemicellulose, chitosan, and galactoglucomannan;
   (b) dissolving a core-forming substance in the solution obtained in step (a), wherein the core-forming substance comprises at least one gas, and wherein said dissolving comprises feeding said gas into the solution obtained in step (a) or pressurizing the solution obtained in step (a) with said gas, thereby dissolving the gas in the solution; and
   (c) precipitating the polymer component and simultaneously forming cores from the core-forming substance by contacting the solution of step (b) with a second solution by transferring the solution of step (b) to the second solution by dripping or spraying, wherein droplets of the solution of step (b) are formed prior to contacting the second solution, wherein the second solution comprises a second solvent of a polar character, and wherein the polymer component is insoluble in the second solvent, thereby forming precipitated polymer shells having an outer diameter of from about 10 µm to about 10 mm around said cores when the solution obtained in step (b) is entering the second solution.

7. The method according to claim 6, wherein the polymer component is cellulose.

8. The method according to claim 6, wherein the second solution comprises a surfactant.

9. The method according to claim 8, wherein the polymer shells are substantially spherical.

10. The method according to claim 6, wherein the first solvent is dimethylacetamide (DMAc) or N-methyl morpholine oxide (NMMO).

11. The method according to claim 6, wherein the second solvent is an aqueous solvent or a polar solvent.

* * * * *